(12) United States Patent
Paschalakis et al.

(10) Patent No.: US 10,719,936 B2
(45) Date of Patent: Jul. 21, 2020

(54) SYSTEM AND METHOD FOR AUTOMATED FUNDUSCOPIC IMAGE ANALYSIS

(71) Applicant: Retinopathy Answer Limited, Bicester (GB)

(72) Inventors: Stavros Paschalakis, Guildford (GB); Miroslaw Bober, Guildford (GB)

(73) Assignee: Retinascan Limited, Banbury (GB)

( * ) Notice: Subject to any disclaimer, the term of this patent is extended or adjusted under 35 U.S.C. 154(b) by 156 days.

(21) Appl. No.: 15/963,716

(22) Filed: Apr. 26, 2018

(65) Prior Publication Data

US 2018/0315193 A1    Nov. 1, 2018

Related U.S. Application Data

(60) Provisional application No. 62/490,977, filed on Apr. 27, 2017.

(51) Int. Cl.
*G06T 7/00* (2017.01)
*G06K 9/00* (2006.01)
(Continued)

(52) U.S. Cl.
CPC .......... *G06T 7/0016* (2013.01); *A61B 3/0025* (2013.01); *A61B 3/12* (2013.01); *A61B 3/14* (2013.01); *A61B 3/145* (2013.01); *G06K 9/0061* (2013.01); *G06K 9/00617* (2013.01); *G06K 9/42* (2013.01); *G06K 9/4671* (2013.01); *G06K 9/6257* (2013.01); *G06K 9/6269* (2013.01); *G06N 3/08* (2013.01); *G06T 7/11* (2017.01); *G01N 2800/16* (2013.01); *G06K 2209/05* (2013.01); *G06T 2207/20081* (2013.01); *G06T 2207/20084* (2013.01); *G06T 2207/30041* (2013.01)

(58) Field of Classification Search
CPC .......... G01N 2800/16; G06K 2209/05; G06K 9/0061; G06K 9/00617; G06K 9/42; G06K 9/4671; G06K 9/6257; G06K 9/6269; G06N 3/08; G06T 2207/20081; G06T 2207/20084; G06T 2207/30041; G06T 7/0016; G06T 7/11
See application file for complete search history.

(56) References Cited

U.S. PATENT DOCUMENTS

| | | |
|---|---|---|
| 5,784,162 A | 7/1998 | Cabib et al. |
| 6,088,099 A | 7/2000 | Cabib et al. |

(Continued)

*Primary Examiner* — Nirav G Patel
(74) *Attorney, Agent, or Firm* — Hoffberg & Associates; Steven M. Hoffberg

(57) ABSTRACT

A system and method of classifying images of pathology. An image is received, normalized, and segmented normalizing the image; into a plurality of regions; A disease vector is automatically determining for the plurality of regions with at least one classifier comprising a neural network. Each of the respective plurality of regions is automatically annotated, based on the determined disease vectors. The received image is automatically graded based on at least the annotations. The neural network is trained based on at least an expert annotation of respective regions of images, according to at least one objective classification criterion. The images may be eye images, vascular images, or funduscopic images. The disease may be a vascular disease, vasculopathy, or diabetic retinopathy, for example.

20 Claims, 10 Drawing Sheets

(51) Int. Cl.

| | | |
|---|---|---|
| *G06K 9/42* | (2006.01) | |
| *G06T 7/11* | (2017.01) | |
| *G06K 9/62* | (2006.01) | |
| *G06N 3/08* | (2006.01) | |
| *A61B 3/00* | (2006.01) | |
| *A61B 3/12* | (2006.01) | |
| *A61B 3/14* | (2006.01) | |
| *G06K 9/46* | (2006.01) | |

(56) References Cited

U.S. PATENT DOCUMENTS

| | | |
|---|---|---|
| 6,198,532 B1 | 3/2001 | Cabib et al. |
| 6,276,798 B1 | 8/2001 | Gil et al. |
| 6,419,361 B2 | 7/2002 | Cabib et al. |
| 6,556,853 B1 | 4/2003 | Cabib et al. |
| 6,895,264 B2 | 5/2005 | Rice et al. |
| 6,943,153 B1 | 9/2005 | Manning, Jr. et al. |
| 6,992,775 B2 | 1/2006 | Soliz et al. |
| 7,433,532 B2 | 10/2008 | Truitt et al. |
| 7,474,775 B2 | 1/2009 | Abramoff et al. |
| 7,712,898 B2 | 5/2010 | Abramoff et al. |
| 7,931,902 B2 | 4/2011 | de Sauvage et al. |
| 8,098,907 B2 | 1/2012 | Yan et al. |
| 8,114,843 B2 | 2/2012 | Isacoff et al. |
| 8,194,936 B2 | 6/2012 | Abramoff et al. |
| 8,207,396 B2 | 6/2012 | Payne et al. |
| 8,303,115 B2 | 11/2012 | Ribaric et al. |
| 8,309,350 B2 | 11/2012 | Isacoff et al. |
| 8,340,437 B2 | 12/2012 | Abramoff et al. |
| 8,705,826 B2 | 4/2014 | Liu et al. |
| 8,787,638 B2 | 7/2014 | Zee et al. |
| 8,879,813 B1 | 11/2014 | Solanki et al. |
| 8,885,901 B1 | 11/2014 | Solanki et al. |
| 8,896,682 B2 | 11/2014 | Bressler et al. |
| 9,002,085 B1 | 4/2015 | Solanki et al. |
| 9,008,391 B1 | 4/2015 | Solanki et al. |
| 9,053,431 B1 | 6/2015 | Commons |
| 9,097,707 B2 | 8/2015 | Isacoff et al. |
| 9,545,196 B2 | 1/2017 | Abramoff et al. |
| 2001/0033364 A1 | 10/2001 | Cabib et al. |
| 2002/0052551 A1 | 5/2002 | Sinclair et al. |
| 2002/0194630 A1 | 12/2002 | Manning, Jr. et al. |
| 2003/0129164 A1 | 7/2003 | Flannery et al. |
| 2004/0221855 A1 | 11/2004 | Ashton |
| 2004/0254154 A1 | 12/2004 | Ashton |
| 2006/0257031 A1 | 11/2006 | Abramoff et al. |
| 2007/0128662 A1 | 6/2007 | Isacoff et al. |
| 2008/0124344 A1 | 5/2008 | Combs et al. |
| 2017/0278289 A1* | 9/2017 | Marino .............. G06T 7/44 |
| 2019/0191988 A1* | 6/2019 | Gargeya .............. A61B 3/12 |

\* cited by examiner

SYSTEM AND METHOD FOR AUTOMATED FUNDUSCOPIC IMAGE ANALYSIS

CROSS REFERENCE TO RELATED APPLICATION

The present application claims priority from U.S. Provisional Patent Application No. 62/490,977, filed Apr. 27, 2017, the entirety of which is expressly incorporated herein by reference.

FIELD OF THE INVENTION

The present invention relates to the field of automated funduscopic image analysis using neural networks ("NN") or deep neural networks ("DNN").

BACKGROUND OF THE INVENTION

Each of the references cited herein are expressly incorporated herein by reference in their entirety.

The human retina is readily photographed using a variety of commonly available specialist cameras. In the UK most opticians, in particular the major chains, have such cameras in their practices already and a retinal photograph is increasingly offered as part of a standard eye test.

Retinal images may be used to assess many eye diseases—or in general retinopathy—and over recent years as the resolution of digital cameras have increased, has become the preferred way to assess retinal health. There are many types of retinopathy which can be detected on the image, from hemorrhages to tumors, and although many such diseases can lead to serious consequences (including blindness), the early stages usually cause no symptoms a patient can detect. As early intervention is often critical to successful management and/or cure, there are a number of compelling public health reasons to make assessing retinal images more routine.

Type II diabetes is a particularly relevant disease, as one of its consequences is the development small bleeds on the retina (micro-aneurysms). If left untreated, these can develop rapidly into serious eye disease, possibly before the patient has been diagnosed as a type II diabetic.

Diabetic retinopathy ("DR") is the leading cause of adult blindness worldwide, including developed countries like the UK. Consequently, the UK-NHS offers all type II diabetes patients a free retinal screen every year, where a digital photo is taken and passed to a grading center and trained graders (humans) examine the image in minute detail for the earliest signs of bleeding. This manual process is costly, but to date is the most reliable way to process these images. Despite years of research, no automated system has yet been able to demonstrate the levels of reliability and accuracy a trained human can achieve.

U.S. 20170039689 discloses "deep learning" technologies for assessing DR from images. See also, U.S. 20170039412, 20150110348, 20150110368, 20150110370, 20150110372, U.S. Pat. Nos. 9,008,391, 9,002,085, 8,885,901, 8,879,813, and 20170046616. Retinal images from a funduscope provide an indication of vascular conditions, and may be useful for diagnosing both eye disease and more generally vascular disease.

"Deep learning" is a refinement of artificial NN ("ANN"), consisting of more than one hidden layer, with that permits higher levels of abstraction and improved predictions from data [2]. See, Greenspan, Hayit, Bram van Ginneken, and Ronald M. Summers. "Guest editorial deep learning in medical imaging: Overview and future promise of an exciting new technique." *IEEE Transactions on Medical Imaging* 35.5 (2016): 1153-1159. Convolutional neural networks ("CNN") are powerful tools for computer vision tasks. Deep CNNs can be formulated to automatically learn mid-level and high-level abstractions obtained from raw data (e.g., images). Generic descriptors extracted from CNNs are effective in object recognition and localization in natural images.

In machine learning, two paradigms, supervised learning and unsupervised learning. In supervised learning, the training data is labelled, that is, there is an extrinsic truth, such that statistical learning is tethered to an external standard. In unsupervised learning, the training data is analyzed without reference to a ground truth, and therefore, the features are intrinsic. In semi-supervised learning techniques, aspects of both paradigms are employed, that is, not all samples (or attributes of samples) of the training data set are labelled.

In medical imaging, the accurate diagnosis and/or assessment of a disease depends on both image acquisition and image interpretation. Image acquisition has improved substantially over recent years, with devices acquiring data at faster rates and increased resolution. The present technology therefore addresses the image interpretation process. Most interpretations of medical images are performed by physicians; however, image interpretation by humans is limited due to its subjectivity, large variations across interpreters, and fatigue.

Human examiners may be inconsistent in their interpretations, and prone to error. Further, different humans may have different standards. Therefore, even obtaining training data is not without difficulty.

Many diagnostic tasks require an initial search process to detect abnormalities, and to quantify measurements and changes over time.

CNNs have been applied to medical image processing, see Sahiner et al. [4]. ROIs containing either biopsy-proven masses or normal tissues were extracted from mammograms. The CNN consisted of an input layer, two hidden layers and an output layer and used backpropagation for training. CNNs have also been applied to lung nodule detection [5], and microcalcifications on mammography [6].

The typical CNN architecture for image processing consists of a series of layers of convolution filters, interspersed with a series of data reduction or pooling layers. The convolution filters are applied to small patches of the input image. Like the low-level vision processing in the human brain, the convolution filters detect increasingly more relevant image features, for example lines or circles that may represent straight edges (such as for organ detection) or circles (such as for round objects like colonic polyps), and then higher order features like local and global shape and texture. The output of the CNN is typically one or more probabilities or class labels. The convolution filters are learned from training data. This is desirable because it reduces the necessity of the time-consuming hand-crafting of features that would otherwise be required to pre-process the images with application-specific filters or by calculating computable features. There are other network architecture variants, such as a deep recurrent neural network ("DRNN") known as long short-term memory [7].

CNNs are parallelizable algorithms, and acceleration of processing (approximately 40 times) is enabled by graphics processing unit (GPU) computer chips, compared to CPU processing alone. See [8]. In medical image processing, GPUs are usable for segmentation, reconstruction, registration, and machine learning [9], [10].

Training a deep CNN ("DCNN") from scratch (or full training) is a challenge. First, CNNs require a large amount of labeled training data, a requirement that may be difficult to meet in the medical domain where expert annotation is expensive and the diseases (e.g., lesions) are scarce. Second, training a DCNN requires large computational and memory resources, without which, the training process would be extremely time-consuming. Third, training a DCNN is often complicated by overfitting and convergence issues, which often require repetitive adjustments in the architecture or learning parameters of the network to ensure that all layers are learning with comparable speed. Given these difficulties, several new learning schemes, termed "transfer learning" and "fine-tuning", are shown to provide solutions and are increasingly gaining popularity. However, empirical adjustments to the process characterize the state of the art, with significant differences in approach, implementation, and results are observed in the art even when using similar algorithms for similar goals. See www.kaggle.com/c/diabetic-retinopathy-detection.

Note that the training of a network cannot be updated, and any change in the algorithm or training data requires re-optimization of the entire network. A new technique provides some mitigation of this constraint, See, U.S. Pat. No. 9,053,431, expressly incorporated herein by reference. Thus, the network may be supplemented after definition, based on a noise or error vector output of the network.

Computer-aided detection (CAD) is a well-established area of medical image analysis that is highly amenable to deep learning. In the standard approach to CAD [11] candidate lesions are detected, either by supervised methods or by classical image processing techniques such as filtering and mathematical morphology. Candidate lesions are often segmented, and described by an often large set of hand-crafted features. A classifier is used to map the feature vectors to the probability that the candidate is an actual lesion. The straightforward way to employ deep learning instead of hand-crafted features is to train a CNN operating on a patch of image data centered on the candidate lesion. A combination of different CNNs is used to classify each candidate.

Various works focus on the supervised CNNs in order to achieve categorization. Such networks are important for many applications, including detection, segmentation and labelling. Other works focus on unsupervised schemes which are mostly shown to be useful in image encoding, efficient image representation schemes and as a pre-processing step for further supervised schemes. Unsupervised representation learning methods such as Restricted Boltzmann Machines (RBM) may outperform standard filter banks because they learn a feature description directly from the training data. The RBM is trained with a generative learning objective; this enables the network to learn representations from unlabeled data, but does not necessarily produce features that are optimal for classification. Van Tulder et al., [18] conducted an investigation to combine the advantages of both generative and a discriminative learning objectives in a convolutional classification restricted Boltzmann machine, which learns filters that are good both for describing the training data and for classification. It is shown that a combination of learning objectives outperforms purely discriminative or generative learning.

CNNs enable learning data-driven, highly representative, layered hierarchical image features. These features have been demonstrated to be a very strong and robust representation in many application domains, as presented in this issue. In order to provide such a rich representation and successful classification, sufficient training data are needed.

When sufficient data are not available, there are several ways to proceed:

Transfer learning: CNN models (supervised) pre-trained from natural image dataset or from a different medical domain are used for a new medical task at hand. In one scheme, a pre-trained CNN is applied to an input image and then the outputs are extracted from layers of the network. The extracted outputs are considered features and are used to train a separate pattern classifier. For instance, in Bar et al. [25], [26] pre-trained CNNs were used as a feature generator for chest pathology identification. In Ginneken et al. [27] integration of CNN-based features with handcrafted features enabled improved performance in a nodule detection system.

Fine Tuning: When a medium sized dataset does exist for the task at hand, one suggested scheme is to use a pre-trained CNN as initialization of the network, following which further supervised training is conducted, of several (or all) the network layers, using the new data for the task at hand. Transfer learning and fine tuning are key components in the use of DCNNs in medical imaging applications.

Shin et al. [17] and Tajbakhsh et al. [28] show that using pre-trained CNNs with fine-tuning achieved the strongest results, and that deep fine-tuning led to improved performance over shallow fine-tuning, and the importance of using fine-tuning increases with reduced size training sets, regardless of specific applications domain (Tajbakhsh et al.), and for all network architectures (Shin et al. [17]). The GoogLeNet architecture led to state-of-the-art detection of mediastinal lymph nodes compared to other less deep architectures, see Shin et al.

The lack of publicly available ground-truth data, and the difficulty in collecting such data per medical task, both cost-wise as well as time-wise, is a prohibitively limiting factor in the medical domain. Though crowdsourcing has enabled annotation of large scale databases for real world images, its application for biomedical purposes requires a deeper understanding and hence, more precise definition of the actual annotation task Nguyen et al. [29], McKenna et al. [30]. The fact that expert tasks are being outsourced to non-expert users may lead to noisy annotations introducing disagreement between users. Likewise, use of uncontrolled clinical outcome data, or user data as a basis for feedback, may lead to poor outcomes, due to lack of standardization and control. Many issues arise in combining the knowledge of medical experts with non-professionals, such as how to combine the information sources, how to assess and incorporate the inputs weighted by their prior-proved accuracy in performance and more. Albarqouni et al. [31] present a network that combines an aggregation layer that is integrated into the CNN to enable learning inputs from the crowds as part of the network learning process. Results shown give valuable insights into the functionality of DCNN learning from crowd annotations. Crowdsourcing studies in the medical domain show that a crowd of nonprofessional, inexperienced users can in fact perform as well as the medical experts, which was observed by Nguyen et al. [29] and McKenna et al. [30] for radiology images. This perhaps means that the results do not capture and exploit the skill, knowledge and insight of the experts.

Unsupervised feature learning for mammography risk scoring is presented in Kallenberg et al. [32]. In this work, a method is shown that learns a feature hierarchy from unlabeled data. The learned features are then input to a simple classifier, and two different tasks are addressed: i)

breast density segmentation, and ii) scoring of mammographic texture, with state-of-the-art results achieved. To control the model capacity, a sparsity regularizer is introduced that incorporates both lifetime and population sparsity. The convolutional layers in the unsupervised parts are trained as autoencoders; In the supervised part the (pretrained) weights and bias terms are fine-tuned using softmax regression.

Yan et al. [33] design a multi-stage deep learning framework for image classification and apply it on body part recognition. In the pre-train stage, a CNN is trained using multi-instance learning to extract the most discriminative and non-informative local patches from the training slices. In the boosting stage, the pre-trained CNN is further boosted by these local patches for image classification. A hallmark of the method was that it automatically discovered the discriminative and non-informative local patches through multi-instance deep learning. Thus, no manual annotation was required.

Regression networks are not very common in the medical imaging domain. In Miao et al. [34], a CNN regression approach is presented, for real-time 2-D/3-D registration. Three algorithmic strategies are proposed to simplify the underlying mapping to be regressed, and to design a CNN regression model with strong non-linear modelling. Results show that the discriminative local (DL) method is more accurate and robust than two state-of-the-art accelerated intensity-based 2-D/3-D registration methods.

Golkov et al. [35] provide an initial proof-of-concept, applying DL to reduce diffusion MRI data processing to a single optimized step. They show that this modification enables one to obtain scalar measures from advanced models at twelve-fold reduced scan time and to detect abnormalities without using diffusion models. The relationship between the diffusion-weighted signal and microstructural tissue properties is non-trivial. Golkov et al. [35] demonstrate that with the use of a DNN such relationships may in fact be revealed: DWIs are directly used as inputs rather than using scalar measures obtained from model fitting. The work shows microstructure prediction on a voxel-by-voxel basis as well as automated model-free segmentation from DWI values, into healthy tissues and MS lesions. Diffusion kurtosis is shown to be measured from only 12 data points and neurite orientation dispersion and density measures from only 8 data points. This may allow for fast and robust protocols facilitating clinical routine and demonstrates how classical data processing can be streamlined by means of deep learning.

Kaggle (www.kaggle.org) organized a competition on detection and staging of DR from color fundus images, and around 80,000 images were made available (www.kaggle.com/c/diabetic-retinopathy-detection). May proposals used NN.

U.S. 2014/0314288 discloses a three stage system that analyzes fundus images with varying illumination and fields of view and generates a severity grade for DR. Image pre-processing includes histogram equalization, contrast enhancement, and dynamic range normalization. In the first stage, bright and red regions are extracted from the fundus image using various combination of global filters and thresholding techniques. An optic disc (OD) has similar structural appearance as bright lesions, and the blood vessel regions have similar pixel intensity properties as the red lesions. Hence, the region corresponding to the optic disc is removed from the bright regions using existing optic disc detection algorithms and the regions corresponding to the blood vessels are removed from the red regions using a simple detection technique. This leads to an image containing bright candidate regions and another image containing red candidate regions. Region-based features are computed, including area, perimeter, solidity, min, mas, mean, standard deviation, etc.; in all, 30 features are used selected by AdaBoost (en.wikipedia.org/wiki/AdaBoost). In the second stage, the bright and red candidate regions are subjected to two-step hierarchical classification. In the first step, bright and red lesion regions are separated from non-lesion regions based on the features. In the second step, the classified bright lesion regions are further classified as hard exudates or cotton-wool spots, while the classified red lesion regions are further classified as hemorrhages and micro-aneurysms. The classifier may take the form of GMM (en.wikipedia.org/wiki/Mixture_model # Gaussian_mixture_model), kNN (en.wikipedia.org/wiki/K-nearest_neighbors_algorithm), SVM (en.wikipedia.org/wiki/Support_vector_machine, en.wikipedia.org/wiki/Supervised_learning), etc. In the third stage, the numbers of bright and red lesions per image are combined to generate a DR severity grade. Such a system aims in reducing the number of patients requiring manual assessment, and in prioritizing eye-care delivery measures for patients with highest DR severity.

U.S. Pat. No. 8,098,907 discloses automatic detection of micro-aneurysms (MAs) by also taking into account information such as location of vessels, optic disc and hard exudates (HEs). The method works by (i) dividing the image into subregions of fixed size, followed by region enhancement/normalization and adaptive analysis, (ii) optic disc, vessel, and HE detection, and (iii) combination of the results of (i) and (ii) above. MA detection is based on top hat filtering and local adaptive thresholding.

U.S. 2015/0104087 discloses automated fundus image side, i.e. left or right eye detection, field detection and quality assessment. The technology uses physiological characteristics such as location of optic disc and macula and the presence of symmetry in the retinal blood vessel structure. Field and side detection are multi-channel or single channel. The algorithm detects the optic disc using normalized 2D cross-correlation using an optic disc template. For high-resolution images, blood vessel structure density is used to determine side and field. The quality for each image is assessed by analysis of the vessel symmetry in the image. This is done by obtaining a binary segmented image of the blood vessels, extracting features and applying a classification algorithm. Quality is a grade of 1 to 5. For vessel binarization, wavelets and edge location refinement are proposed. This is followed by morphological operations. For feature extraction, the image is divided into 20 rectangular windows, and local vessel density (LVD) is computed as the number of non-zero pixels in window. The 20 LVDs are normalized by a global vessel density (GVD) computed as the number of non-zero pixels for a segmented binary image of grade 5. A feature vector is formed by the LVDs and GVD of the image. For classification, SVM is proposed. Image registration and similar techniques to the above can be used to assign quality levels to overlapping stitched images.

U.S. Pat. Nos. 8,879,813, 8,885,901, 9,002,085, 9,008, 391, U.S. 2015/0110348, U.S. 2015/0110368, U.S. 2015/0110370, U.S. 2015/0110372, U.S. 2017/0039412, and U.S. 2017/0039689 disclose various aspects of a diagnostic system. A retinal image may be enhanced based on median normalization, to locally enhance the image at each pixel location using local background estimation. Active pixels are detected in retina images, based on median filtering/dilation/erosion/etc. Essentially, this detects the retina disc and eliminates pixels close to the border. Regions of interest are detected. Descriptors of local regions are extracted, e.g., by computing two morphologically filtered images with the morphological filter computed over geometric shaped local regions of two different types or sizes, and taking their difference. Image quality is assessed using computer vision techniques to assess appropriateness for grading. Images are automatically screened for diseases. Image-based lesion biomarkers are automatically analyzed, over different visits of a patient, with image registration between visits. Changes in lesions and anatomical structures are computed, and quantified it terms of statistics wherein the computed statistics represent the image-based biomarker that can be used for monitoring progression, early detection, and/or monitoring effectiveness of treatment therapy.

U.S. Pat. No. 8,879,813 describe automated detection of active pixels in retina images by accessing a retina image, generating two median filtered versions with different window sizes, generating a difference image from the filtered versions, and then generating a binary image.

U.S. Pat. No. 8,885,901 describe enhancing a retina image by accessing a retina image, filtering it with a median filter and modifying the values in the original image based on the values in the original and filtered images, wherein the enhanced image is used for detecting a medical condition.

U.S. Pat. No. 9,002,085 and U.S. 2015/0110372 describe generating descriptors of local regions in a retina image by accessing a retina image, generating two morphologically filtered versions, the first with a circular/regular polygon window and the second with an elongated/elliptical window, generating difference values from the filtered images and using them as pixel descriptor values for the retina image.

U.S. Pat. No. 9,008,391 and U.S. 2015/0110368 describe accessing retina images for a patient, for each of the images designating a subset of pixels as active including regions of interest, computing pixel-level descriptors, providing pixel level classification from the descriptors using supervised learning, computing a second descriptor, and providing a second classification for a plurality of pixels using supervised learning.

U.S. 2015/0110348 and U.S. 2017/0039412 describe automated detection of regions of interest (ROIs) in retina images by accessing a retina image, extracting regions with one or more desire properties using multiscale morphological filterbank analysis, and storing a binary map.

U.S. 2015/0110370 and U.S. 2017/0039689 describe enhancing a retinal image by accessing a funduscopic image, estimating the background at single of multiple scales, and scaling the intensity at a first pixel location adaptively based on the intensity at the same position in the background image.

REFERENCES

[1] *MIT Technol. Rev.*, 2013. Available: www.technologyreview.com/s/513696/deep-learning
[2] Y. LeCun, Y. Bengio, and G. Hinton, "Deep learning," *Nature, vol.* 521, no. 7553, pp. 436-444, 2015.
[3] J. Schmidhuber, "Deep learning in neural networks: An overview," *Neural Netw.*, vol. 61, pp. 85-117, 2015.
[4] B. Sahiner et al., "Classification of mass and normal breast tissue: A convolution neural network classifier with spatial domain and texture images," *IEEE Trans. Med. Imag.*, vol. 15, no. 5, pp. 598-610, Oct. 1996.
[5] S. C. B. Lo, J. S. J. Lin, M. T. Freedman, and S. K. Mun, "Computerassisted diagnosis of lung nodule detection using artificial convolution neural-network," *Proc. SPIE Med. Imag., Image Process.*, vol. 1898, pp. 859-869, 1993.
[6] H.-P. Chan, S.-C. Lo, B. Sahiner, K. L. Lam, and M. A. Helvie, "Computer-aided detection of mammographic microcalcifications: Pattern recognition with an artificial neural network," *Med. Phys.*, vol. 22, no. 10, pp. 1555-67, 1995.
[7] S. Hochreiter and J. Schmidhuber, "Long short-term memory," *Neural Comput.*, vol. 9, no. 8, pp. 1735-1780, 1997.
[8] G. E. Hinton, S. Osindero, and Y. W. Teh, "A fast learning algorithm for deep belief nets," *Neural Comput.*, vol. 18, no. 7, pp. 1527-1554, 2006.
[9] D. Castano-Diez, D. Moser, A. Schoenegger, S. Prugnaller, and A. S. Frangakis, "Performance evaluation of image processing algorithms on the GPU," *J. Struct. Biol.*, vol. 164, no. 1, pp. 153-160, 2008.
[10] A. Eklund, P. Dufort, D. Forsberg, and S. M. LaConte, "Medical image processing on the GPU-Past, present and future," *Med. Image Anal.*, vol. 17, no. 8, pp. 1073-94, 2013.
[11] B. van Ginneken, C. M. Schaefer-Prokop, and M. Prokop, "Computeraided diagnosis: How to move from the laboratory to the clinic," *Radiol.*, vol. 261, no. 3, pp. 719-732, 2011.
[12] A. Setio et al., "Pulmonary nodule detection in CT images using multiview convolutional networks," *IEEE Trans. Med. Imag.*, vol. 35, no. 5, pp. 1160-1169, May 2016.
[13] H. Roth et al., "Improving computer-aided detection using convolutional neural networks and random view aggregation," *IEEE Trans. Med. Imag.*, vol. 35, no. 5, pp. 1170-1181, May 2016.
[14] Q. Dou et al., "Automatic detection of cerebral microbleeds from MR images via 3D convolutional neural networks," *IEEE Trans. Med. Imag.*, vol. 35, no. 5, pp. 1182-1195, May 2016.
[15] K. Sirinukunwattana et al., "Locality sensitive deep learning for detection and classification of nuclei in routine colon cancer histology images," *IEEE Trans. Med. Imag.*, vol. 35, no. 5, pp. 1196-1206, May 2016.
[16] M. Anthimopoulos, S. Christodoulidis, A. Christe, and S. Mougiakakou, "Lung pattern classification for interstitial lung diseases using a deep convolutional neural network," *IEEE Trans. Med. Imag.*, vol. 35, no. 5, pp. 1207-1216, May 2016.
[17] H.-C. Shin et al., "Deep convolutional neural networks for computeraided detection: CNN architectures, dataset characteristics and transfer learning," *IEEE Trans. Med. Imag.*, vol. 35, no. 5, pp. 1285-1298, May 2016.
[18] G. van Tulder and M. de Bruijne, "Combining generative and discriminative representation learning in convolutional restricted Boltzmann machines," *IEEE Trans. Med. Imag.*, vol. 35, no. 5, pp. 1262-1272, May 2016.
[19] A. Depeursinge et al., *Comput. Med. Imag. Graph.*, vol. 36, no. 3, pp. 227-238, 2012.
[20] F. Ghesu et al., "Marginal space deep learning: Efficient architecture for volumetric image parsing," *IEEE Trans. Med. Imag., vol.* 35, no. 5, pp. 1217-1228, May 2016.
[21] T. Brosch et al., "Deep 3D convolutional encoder networks with shortcuts for multiscale feature integration applied to multiple sclerosis lesion segmentation," *IEEE Trans. Med. Imag., vol.* 35, no. 5, pp. 1229-1239, May 2016.

[22] S. Pereira, A. Pinto, V. Alves, and C. Silva, "Brain tumor segmentation using convolutional neural networks in MRI images," *IEEE Trans. Med. Imag.*, vol. 35, no. 5, pp. 1240-1251, May 2016.

[23] P. Moeskops et al., "Automatic segmentation of MR brain images with a convolutional neural network," *IEEE Trans. Med. Imag.*, vol. 35, no. 5, pp. 1252-1261, May 2016.

[24] M. van Grinsven, B. van Ginneken, C. Hoyng, T. Theelen, and C. Sanchez, "Fast convolutional neural network training using selective data sampling: Application to hemorrhage detection in color fundus images," *IEEE Trans. Med. Imag.*, vol. 35, no. 5, pp. 1273-1284, May 2016.

[25] Y. Bar, I. Diamant, L. Wolf, and H. Greenspan, "Deep learning with non-medical training used for chest pathology identification," *Proc. SPIE Med. Imag. Computer-Aided Diagnosis*, vol. 9414, 2015.

[26] Y. Bar, I. Diamant, L. Wolf, S. Lieberman, E. Konen, and H. Greenspan, "Chest pathology detection using deep learning with non-medical training," in *Proc. IEEE 12th Int. Symp. Biomed. Imag.*, 2015, pp. 294-297.

[27] B. van Ginneken, A. A. Setio, C. Jacobs, and F. Ciompi, "Off-the-shelf convolutional neural network features for pulmonary nodule detection in computed tomography scans," in *Proc. IEEE 12th Int. Symp. Biomed. Imag.*, 2015, pp. 286-289.

[28] N. Tajbakhsh et al., "Convolutional neural networks for medical image analysis: Full training or fine tuning?," *IEEE Trans. Med. Imag.*, vol. 35, no. 5, pp. 1299-1312, May 2016.

[29] T. B. Nguyen et al., "Distributed human intelligence for colonic polyp classification in computer-aided detection for CT colonography," *Radiology*, vol. 262, no. 3, pp. 824-833, 2012.

[30] M. T. McKenna et al., "Strategies for improved interpretation of computer-aided detections for CT colonography utilizing distributed human intelligence," *Med. Image Anal.*, no. 6, pp. 1280-1292, 2012.

[31] S. Albarqouni, C. Baur, F. Achilles, V. Belagiannis, S. Demirci, and N. Navab, "Agg-Net: Deep learning from crowds for mitosis detection in breast cancer histology images," *IEEE Trans. Med. Imag.*, vol. 35, no. 5, pp. 1313-1321, May 2016.

[32] M. Kallenberg et al., "Unsupervised deep learning applied to breast density segmentation and mammographic risk scoring," *IEEE Trans. Med. Imag.*, vol. 35, no. 5, pp. 1322-1331, May 2016.

[33] Z. Yan et al., "Multi-instance deep learning: Discover discriminative local anatomies for bodypart recognition," *IEEE Trans. Med. Imag.*, vol. 35, no. 5, pp. 1332-1343, May 2016.

[34] S. Miao, Z. J. Wang, and R. Liao, "A CNN regression approach for real-time 2D/3D registration," *IEEE Trans. Med. Imag.*, vol. 35, no. 5, pp. 1352-1363, May 2016.

[35] V. Golkov et al., "q-Space deep learning: Twelve-fold shorter and model free diffusion MRI scans," *IEEE Trans. Med. Imag.*, vol. 35, no. 5, pp. 1344-1351, May 2016.

[36] K. He, X. Zhang, S. Ren, and J. Sun, Deep residual learning for image recognition ArXiv, 2015, arXiv: 1512.03385, to be published

[37] H. R. Roth et al., "A new 2.5 d representation for lymph node detection in CT," *Cancer Imag. Arch.*, 2015 dx.doi.org/10.7937/K9/TCIA.2015.AQIIDCNM

[38] H. R. Roth et al., "Data from pancreas-CT," *Cancer Imag. Arch.*, 2016 [Online]. Available: dx.doi.org/10.7937/K9/TCIA.2016. tNB1kqBU See, U.S. Pat. Nos. 5,784,162; 6,088,099; 6,198,532; 6,276,798; 6,419,361; 6,556,853; 6,895,264; 6,943,153; 6,992,775; 7,433,532; 7,474,775; 7,712,898; 7,931,902; 8,098,907; 8,114,843; 8,194,936; 8,207,396; 8,303,115; 8,309,350; 8,340,437; 8,705,826; 8,787,638; 8,879,813; 8,885,901; 8,896,682; 9,002,085; 9,008,391; 9,097,707; 9,545,196; 20010033364; 20020052551; 20020194630; 20030129164; 20040221855; 20040254154; 20060257031; 20070128662; 20080124344; 20100061601; 20100172871; 20100220906; 20100302507; 20110097330; 20110173708; 20110242306; 20120190094; 20120257164; 20120272341; 20130108131; 20130116670; 20130137113; 20130301889; 20140023692; 20140199277; 20140276025; 20150110348; 20150110368; 20150110370; 20150110372; 20150124216; 20150224193; 20150238767; 20150379708; 20160120404; 20160217586; 20170039412; 20170039689; 20170046616

SUMMARY OF THE INVENTION

The present invention provides a system and method for automatically predicting presence of vascular disease based on one or more vascular images. The images are preferably funduscopic images, and the vascular disease would then be a retinal disease, or retinopathy. In particular, screening for DR is a particular target for application of the technology.

The underlying methodology is not limited to retinal images, though the visibility of the retinal vasculature in a funduscopic image makes this particularly preferred. However, other vasculature and microvasculature may be analyzed. For example, capillaries of bucchal and sublingual mucosa, intestinal mucosa, sclera, etc., can be imaged under various circumstances.

Retinopathy may be diagnosed as (H35.0) Hypertensive retinopathy-burst blood vessels, due to long-term high blood pressure en.wikipedia.org/wiki/Hypertensive_retinopathy; (H35.0/E10-E14) Diabetic retinopathy-damage to the retina caused by complications of diabetes mellitus, which could eventually lead to blindness en.wikipedia.org/wiki/Diabetic_retinopathy; (H35.0-H35.2) Retinopathy-general term referring to non-inflammatory damage to the retina en.wikipedia.org/wiki/Retinopathy; (H35.1) Retinopathy of prematurity-scarring and retinal detachment in premature babies en.wikipedia.org/wiki/Retinopathy_of_prematurity; (H35.3) Age-related macular degeneration-the photosensitive cells in the macula malfunction and over time cease to work; (H35.3) Macular degeneration-loss of central vision, due to macular degeneration (e.g., Bull's Eye Maculopathy, chloroquine retinopathy en.wikipedia.org/wiki/Chloroquine_retinopathy) en.wikipedia.org/wiki/Macular_degeneration; (H35.3) Epiretinal membrane-a transparent layer forms and tightens over the retina en.wikipedia.org/wiki/Epiretinal_membrane; (H35.4) Peripheral retinal degeneration en.wikipedia.org/wiki/Lattice_degeneration; (H35.5) Hereditary retinal dystrophy en.wikipedia.org/wiki/Progressive_retinal_atrophy; (H35.5) Retinitis pigmentosa-genetic disorder; tunnel vision preceded by night-blindness en.wikipedia.org/wiki/Retinitis_pigmentosa; (H35.6) Retinal haemorrhage; (H35.7) Separation of retinal layers en.wikipedia.org/wiki/Retinal_haemorrhage (e.g., Central serous retinopathy en.wikipedia.org/wiki/Central_serous_retinopathy, Retinal detachment: Detachment of retinal pigment epithelium en.wikipedia.org/wiki/Retinal_detachment) en.wikipedia.org/wiki/Retina # Anatomy_of_vertebrate_retina; (H35.8) Other specified retinal disorders; (H35.81) Macular edema-distorted central vision, due to a swollen macula en.wikipedia.org/wiki/Macular_edema; and (H35.9) Retinal disorder, unspecified. See, World Health Organization ICD-10 codes: Diseases of the eye and adnexa (H00-H59).

The images may be analyzed for various diseases concurrently. For example, the training data may encode signs of at least cotton wool spots (areas of retinal ischemia with edema); hard exudates (fatty deposits); Microaneurysms (appearing as small red dots on the retina); small flame hemorrhages from damaged blood vessel walls; neovascularization: signs of new blood vessel formation on the back of the eye; diabetes—also a cause of early cataracts, due to excess glucose interfering with the metabolism of the crystalline lens, and other clinical signs; see, patient.info/doctor/eye-in-systemic-disease; www.ncbi.nlm.nih.gov/books/NBK221/.

More particularly, the invention comprises a system and method for the automatic detection and localization of DR lesions in retinal fundus images and the automatic DR classification of retinal fundus images. The system recognizes DR based on training data representing classification of regions of patient funduscopic images by experts.

In some embodiments, a computer-implemented method includes analyzing a retinal image and detecting areas of interest in said retinal image. In some embodiments, the method further includes classifying a retinal image based on the detection of the one or more areas of interest.

The present technology provides a new approach to the problem of automatically detecting retinopathy in retinal images. The idea is to collect many thousands of retinal photos which have had all retinopathy marked by human experts, which are annotated by experts, wherein the annotations are validated as being reliable. The annotations take the form of regional assessment of medical classification, as well as image quality. The image quality may also be determined, at least in part, by an unsupervised NN, since the image itself is governed by optical principles. However, some aspects, may benefit from human expertise.

The annotations are used to train a NN, which may be a CNN or DNN. Because of the regional classification of the training data, the network according to the present technology determines a classification of respective regions of a previously unclassified image. This is in contrast to technologies that classify unknown images as a whole. It is therefore apparent that the NN itself is fundamentally dependent on both the labels and what is being labelled.

The training data employ may be the entire retinal image with regional classifications associated as labels, though this increases the degrees of freedom of the input data set, which may complicate the problem without corresponding improvement of network performance. That is, retinopathy in one region of the retina is very similar to retinopathy in other regions, and therefore the training need not be region-specific. Of course, there may indeed be region-specificity, and the present technology does not ignore or disclaim this, and rather finds that adequate performance is achievable while making the region-independent presumption. For example, in a 1000×1000 input image, there are $10^6$ pixels, and without simplification, a NN would have to have at least $10^6$ input neurons. On the other hand, 64×64 pixel regions provide sufficient precision to identify pathology, requiring at least 4096 input neurons, about 250× fewer. Likewise, the region-independent presumption may permit reduction in at least an entire hidden layer of the network which is designed to process regional differences.

Prior to processing, the image may be normalized with respect to color, brightness, etc., in a deterministic statistical or rule-based process. While this normalization may be achieved within the NN, this can also be achieved independent of the network, leading to a simpler implementation of the network.

In some cases, the regions may be normalized after segmentation, or as part of the segmentation process. This permits segmentation to be based on a statistical or rule based process that establishes regional boundaries on a basis other than shape or space. Again, normalization preceding the NN simplifies the NN implementation, but also relieves the NN of learning the pre-normalized features. By employing expert determination of features that may be extracted from the image by a normalization process, the specificity of the NN for the features which are not normalized is increased.

Each retinal image is highly individual, like a fingerprint, so the dataset will never contain an exact match to the whole image. However, the early disease processes targeted by this technology are characterized by being small and localized—a few pixels wide in a high-resolution image. In fact, the reason digital photos have only recently been clinically accepted for screening is that the resolution required to see the earliest signs of disease has only recently been easily available. So the dataset is actually a set of small patches taken from real retinal photos, and the system according to the present technology compares small patches from the new image to the patches in the dataset.

At a high level, given a new image is processed as follows:

Accept raw image from camera, standardize size to 1024×1024 with circular mask.

The NN is implemented to provide a classifier, which operates on the regions. Preferably, the same preprocessing that is applied to the labelled dataset images is applied to unknown images, including the segmentation into regions. The segmented regions, after normalization, are then classified based on the training data. The classifications are then transferred back to the unknown image as a whole, to annotate the unknown image, which is then diagnosed or graded based on the full set of classifications.

The grading may be accompanied by a reliability, which may include an indication of type I (false positive) and/or type II (false negative) errors, and perhaps other types of errors. The grading reliability may also be responsive to original image quality, such as brightness, focus, contrast, color, etc. Where, for example, a portion of the image is of poor quality, the portion that is available for assessment may be analyzed, with a grade and accompanying reliability that assesses the probability of a missed disease-positive diagnosis, and a probability of an erroneous disease-positive diagnosis.

Results can be optionally collated into an overall recommendation, or details can be supplied together with notes about particular areas of concern.

This technique requires collection of sufficient images, suitably assessed by human experts, to form the dataset. The matching algorithm needs to be sufficiently accurate and precise to avoid false positive and false negative results.

Retinal camera models produce images with various resolutions, and the typical retinal lesion will vary in size too. After significant experimentation, reference to experts and UK NHS standards documentation, it was concluded the smallest resolution which would retain sufficient features was 1024×1024 pixels, and the smallest patch in which a target lesion was still identifiable (on such an image) was 32×32 pixels.

The images may be provided in conjunction with additional medical data, such as blood sugar, age, sex, weight, clinical history, etc., and this may be used as part of the classification, though in some cases, it is better to classify the mage, and permit a clinician to integrate the other patient data into a diagnosis and/or prognosis. Indeed, to the extent that a clinician uses the output of the classifier, using clinical data extrinsic to the image for classifying the image risks significant bias downstream where these same factors may be considered again.

The precise balance needed between type I and II errors, as outlined above, will depend on the intended use of the system. For a hospital setting minimizing type II error may be the most important, while for general screening via opticians it might be most important to minimize type I error and avoid causing needless worry to customers.

It is noted that the system need not be limited to full automated diagnosis. Thus, if the Type II errors are minimized, false positives may then be rescreened by another method, such as human grader, or an alternate or supplemental automated analysis, which, for example, might take more time and/or resources. For example, in cases where hash errors are responsible for diminished performance quality, an automated analysis using less data reduction may be employed as a follow-up. Any system, no matter how inherently good or bad, can be "tuned" to strike a different trade-off between these two types of error.

The algorithm was found to be highly effective at marking regions of the retinal image with indications of disease, demonstrating that the image processing/region matching technology was effective and efficient.

Widefield and ultra-widefield retinal images capture fields of view of the retina in a single image that are larger than 45-50 degrees typically captured in retinal fundus images. These images are obtained either by using special camera hardware or by creating a montage using retinal images of different fields. The systems and methods described herein can apply to widefield and ultra-widefield images.

Fluorescein angiography involves injection of a fluorescent tracer dye followed by an angiogram that measures the fluorescence emitted by illuminating the retina with light of wavelength 490 nanometers. Since the dye is present in the blood, fluorescein angiography images highlight the vascular structures and lesions in the retina. The systems and methods described herein can apply to fluorescein angiography images.

It is therefore an object to provide a method of classifying vascular images, comprising: receiving a vascular image; normalizing the vascular image; segmenting the normalized vascular image into a plurality of regions; automatically determining a vasculopathy vector for the plurality of regions with at least one classifier comprising a NN; automatically annotating each of the respective plurality of regions, based on the determined vasculopathy vectors; and automatically grading the received vascular image based on at least the annotations, wherein the NN is trained based on at least an expert annotation of respective regions of vascular images, according to at least one objective classification criterion.

It is also an object to provide a system for classifying vascular images, comprising: an input configured to receive at least one vascular image; a memory con figured to store information defining a NN trained based on at least an expert annotation of respective regions of a plurality of retinal images, according to at least one objective classification criterion; at least one automated processor, configured to: normalize the vascular image; segment the normalized vascular image into a plurality of regions; determine a vasculopathy vector for the plurality of regions with at least one classifier comprising the defined NN; annotate each of the respective plurality of regions, based on the determined vasculopathy vectors; and grade the received vascular image based on at least the annotations; and an output configured to communicate the grade.

It is a still further object to provide a computer readable medium, storing instructions for controlling at least one automated processor, comprising: instructions for normalizing a received vascular image; instructions for segmenting the normalized vascular image into a plurality of regions; instructions for determining a vasculopathy vector for the plurality of regions with at least one classifier comprising a NN; instructions for automatically annotating each of the respective plurality of regions, based on the determined vasculopathy vectors; and instructions for automatically grading the received vascular image based on at least the annotations, wherein the NN is trained based on at least an expert annotation of respective regions of vascular images, according to at least one objective classification criterion.

A further object provides a method of classifying retinal images for presence of retinopathy, comprising: receiving a funduscopic image; automatically normalizing the funduscopic image with respect to at least a tricolor stimulus image space; automatically segmenting the normalized vascular image into a plurality of regions based on at least one segmentation rule; automatically determining a retinopathy vector for the plurality of regions with at least one classifier comprising a NN, the NN being trained based on a training comprising at least a set of funduscopic images having regional expert retinopathy annotations; automatically annotating each of the respective plurality of regions, based on the determined vasculopathy vectors; automatically determining a grade of retinopathy of the received vascular image based on at least the annotations; and outputting the automatically determined grade of retinopathy.

Another object provides a method of classifying eye images, comprising receiving and normalizing an eye image; segmenting the normalized eye image into a plurality of regions; automatically determining an eye disease vector for the plurality of regions with a classifier comprising a NN; automatically annotating each of the respective plurality of regions, based on the determined eye disease vectors; and automatically grading the received eye image based on at least the annotations, wherein the NN is trained based on at least an expert annotation of respective regions of eye images, according to at least one objective classification criterion.

A still further object provides a system for classifying eye images, comprising an input configured to receive at least one eye image; a memory configured to store information defining a NN trained based on at least an expert annotation of respective regions of a plurality of retinal images, according to at least one objective classification criterion; at least one automated processor, configured to: normalize the eye image; segment the normalized eye image into a plurality of regions; determine an eye disease vector for the plurality of regions with at least one classifier comprising the defined NN; annotate each of the respective plurality of regions, based on the determined eye disease vectors; and grade the received eye image based on at least the annotations; and an output configured to communicate the grade.

An object provides a computer readable medium, storing instructions for controlling an automated processor, for normalizing a received eye image; instructions for segmenting the normalized eye image into a plurality of regions; instructions for determining an eye disease vector for the plurality of regions with at least one classifier comprising a NN; instructions for automatically annotating each of the respective plurality of regions, based on the determined eye disease vectors; and instructions for automatically grading the received eye image based on at least the annotations, wherein the NN is trained based on at least an expert annotation of respective regions of eye images, according to at least one objective classification criterion.

A further object provides a method of classifying images of pathology, comprising: receiving an image; normalizing the image; segmenting the normalized image into a plurality of regions; automatically determining a disease vector for the plurality of regions with at least one classifier comprising a NN; automatically annotating each of the respective plurality of regions, based on the determined disease vectors; and automatically grading the received image based on at least the annotations, wherein the NN is trained based on at least an expert annotation of respective regions of images, according to at least one objective classification criterion.

The NN may comprise a plurality of hidden layers, a DNN, RNN, and/or a CNN. The method may further comprise receiving a second vascular image acquired at a time different from the vascular image; and outputting information dependent on at least a change in the vascular image over time.

The NN may be further trained based on at least an expert annotation of a quality of respective regions of a retinal image.

The at least one classifier may comprise a multi-class support vector machine classifier, or a Gradient Boosting Classifier, for example.

The at least one classifier may classify a respective region based on the vasculopathy vectors of a plurality of respective regions, or a plurality of contiguous regions.

The classifier may comprise a classifier for determining a region having indicia of DR.

The grading may comprise grading a degree of DR. The grade may be accompanied by a probability of correctness of the grade. The probability of correctness may comprise a probability of a type I error and a probability of a type II error.

The method may further comprise outputting an image representing the classification of regions of the Vascular image.

The vascular images may comprise funduscopic images. The annotations may comprise indications of DR within a respective region of a respective funduscopic image.

DETAILED DESCRIPTION OF THE PREFERRED EMBODIMENTS

Figure 1:
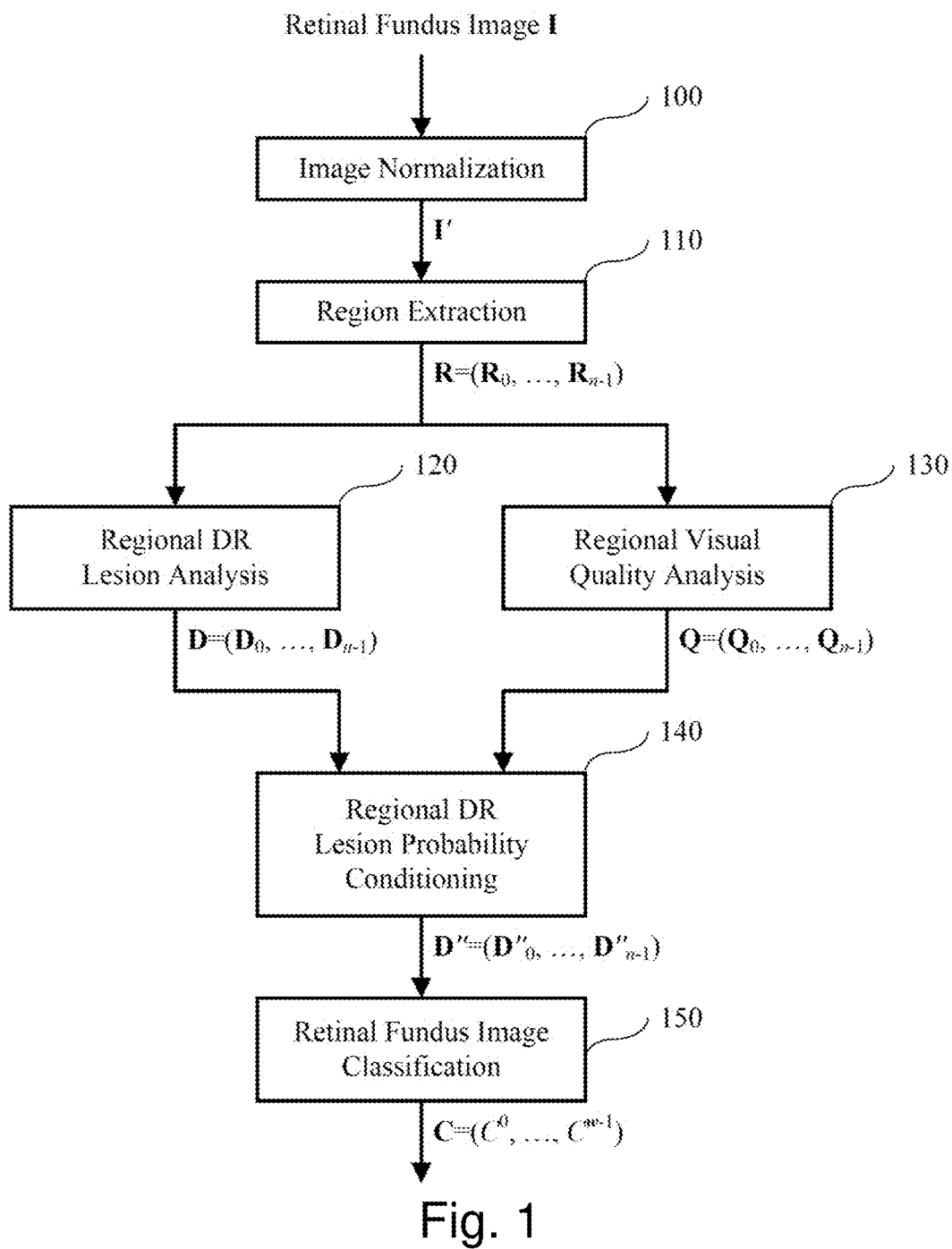
FIG. 1 shows a flowchart according to an embodiment of the invention.
Figure 2A:
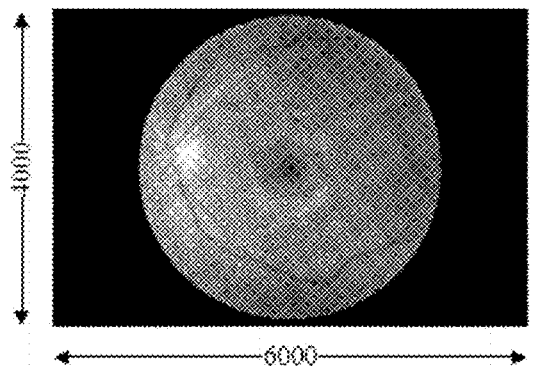
FIGS. 2A-2D show retinal images.
Figure 2B:
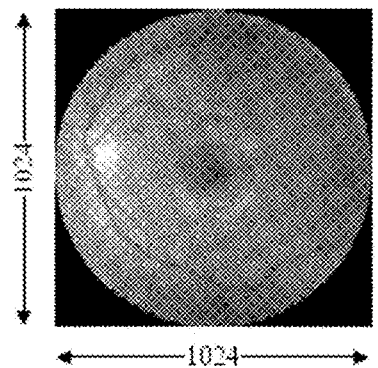
Figure 2C:
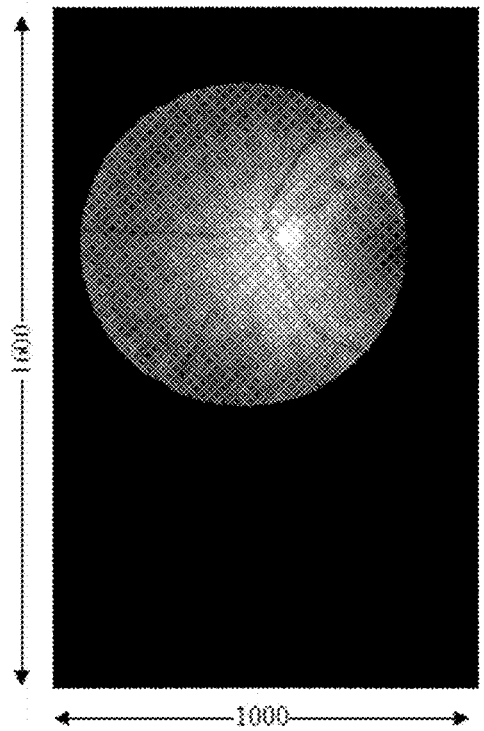
Figure 2D:
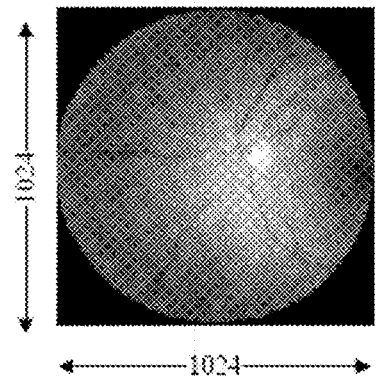

FIG. 1 illustrates an embodiment of the invention. Given a retinal fundus image I, block 100 performs image normalization to produce a normalized image I'. This normalization step involves identifying the retinal disc in I and resizing it to a fixed size, i.e., to a diameter of p pixels in an image of p×p pixels, where, typically, p=1024. This is illustrated in FIGS. 2A-2D, where FIGS. 2A and 2C show pre-normalized retinal fundus images I and FIGS. 2B and 2D show the corresponding normalized retinal fundus images I'. Automatic detection of the retinal disc is a straightforward task which entails the detection of a relatively bright disc on a relatively dark and uniform background. As such, a number of well-known image processing techniques may be used, such as edge detection, circular Hough transform, etc. More details of such techniques may be found in Russ, John C. The image processing handbook. CRC press, 2016.

Next, in block 110 of FIG. 1, retinal regions are extracted from normalized image I'. This process entails extracting small retinal regions from the retinal disc. In some embodiments of the invention these regions may be fully contained in the retinal disk, while in other embodiments of the invention these regions may be partially contained in the retinal disk, for example containing at least 50% or 75% of retinal pixels. In some embodiments of the invention these regions may be circular and with a diameter of q pixels, where q=32 or q=64, while in other embodiments of the invention these regions may be square and with size q×q pixels, where q=32 or q=64. In alternative embodiments of the invention, a different region geometry may be used, for example a hexagon region.

More generally, a continuous region of pixels is defined, of arbitrary geometry. Indeed, in some cases, the region may be topologically discontiguous, or the analysis may be of the image information in a domain other than pixels.

Figure 3:
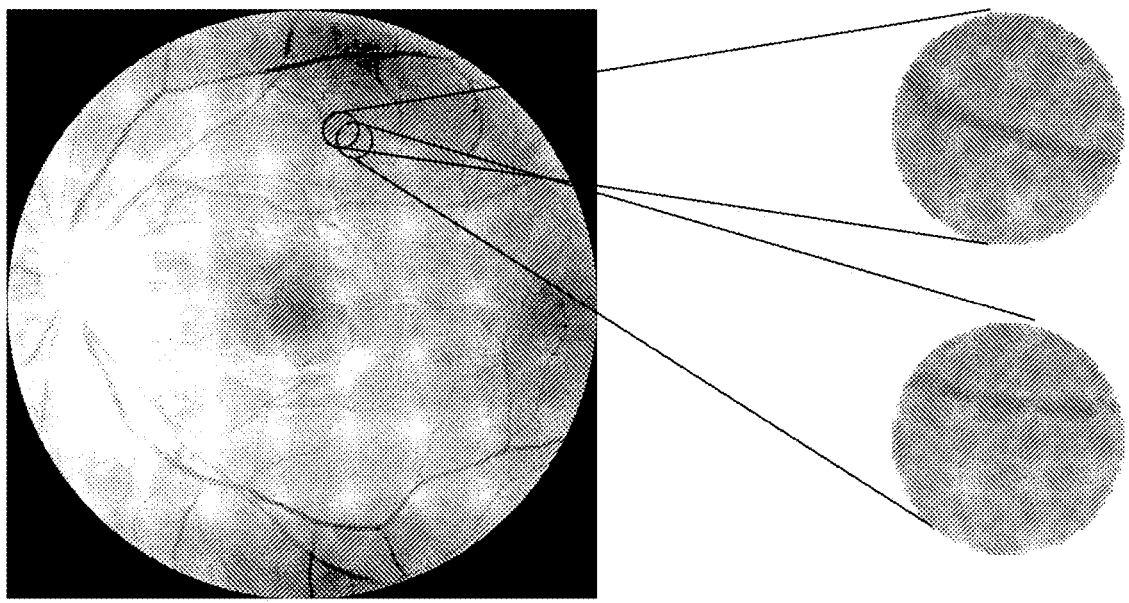
FIGS. 3 and 4 show a retinal image and round and square regions thereof, respectively.
Figure 4:
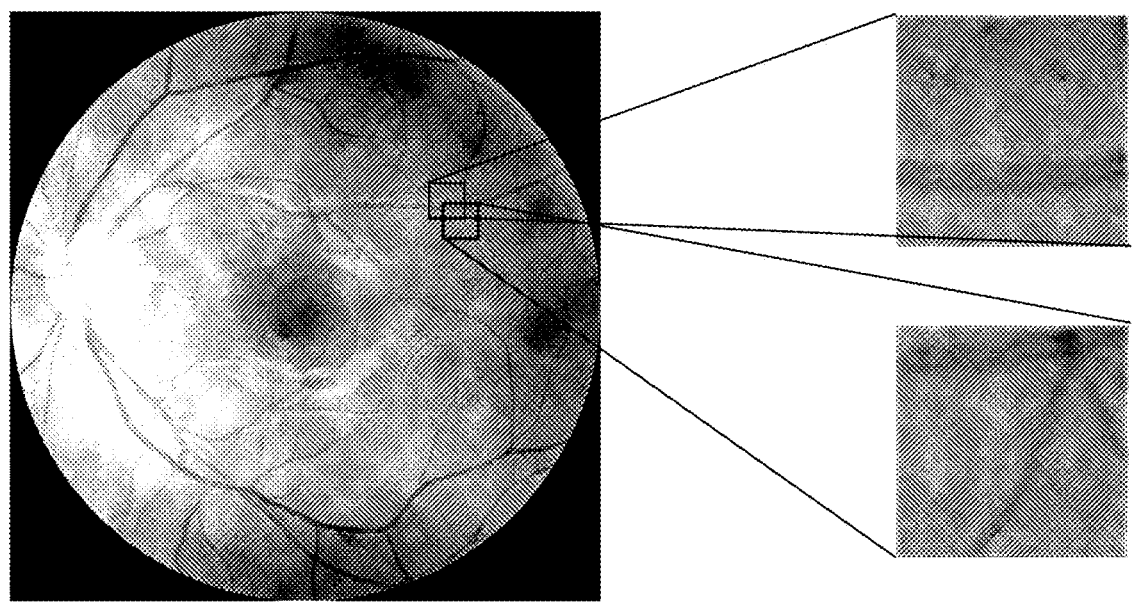

FIG. 3 illustrates the extraction of two circular retinal regions $R_\alpha = R(x,y)$ centered on $(x,y)=(579,209)$ and $R_\beta = R(x,y)$ centered on $(x,y)=(603,226)$ from a normalized image I', while FIG. 4 illustrates the extraction of two square retinal regions $R_\alpha = R(x,y)$ centered on $(x,y)=(757,327)$ and $R_\beta = R(x,y)$ centered on $(x,y)=(782,363)$ from a normalized image I'. In all cases, the regions are typically extracted in a regular pattern and with a significant degree of overlap; for example starting at the top-most left-most region, extract successive regions by moving with a stride of s pixels to the right up to the top-most right-most region, then move s pixels down, extract successive regions from the left-most to the right-most moving right by s pixels, and so on. Typically s takes a low value, i.e. typically between 1 and a few pixels. Different embodiments of the invention may use a higher value for s and/or may extract non-overlapping regions. In all cases, block 110 produces a set of n retinal regions $R_0, \ldots, R_{n-1}$, collectively denoted by R and with $R_k = R(x,y)$ denoting a region centered on (x,y) of normalized image I'.

We now consider the operation of block 120 of FIG. 1. Block 120 of FIG. 1 analyzes all the retinal regions independently and for each region $R_k$ produces a DR lesion classification vector $D_k = (D_k^0, \ldots, D_k^{l-1})$ where l is the number of classes that the classifier of block 120 has been trained on and $D_k^c$ is the class membership probability of region k for class c.

As a first example, in one embodiment of the invention, the classifier in block 120 may be trained to classify regions to l=2 classes, with c=0 the "Healthy" class label and c=1 the "Diseased" class label.

As a second example, in a different embodiment of the invention, the classifier in block 120 may be trained to classify regions to l>2 classes, with c=0 the "Healthy" class label, c=1 the "Micro Aneurism" class label, c=2 the "Hard Exudate" class label, ..., c=l−1 the "Laser Scar" class label. Thus, in such an embodiment, different types of lesions, artifacts or scars that may be present in the retinal fundus image are assigned separate class labels.

Thus, different embodiments of the invention may employ classifiers trained on different numbers of classes to achieve the highest possible performance in detecting DR lesions and/or identifying the types of detected DR lesions. In all cases, in alternative embodiments of the invention, the classifier in block 120 may be configured to output $D_k^c$ as a binary 0 or 1 value rather than a class membership probability, in which case $D_k$ is not a class probability distribution but a classification decision vector.

We now consider the architecture of block 120 of FIG. 1 in more detail. In one embodiment of the invention, block 120 of FIG. 1 comprises the architecture illustrated in FIG. 5. In block 500, retinal regions are optionally normalized. This optional normalization may, for example, involve mean subtraction, resulting in the mean intensity of each color channel of each retinal region taking a value of 0, or some other mean adjustment, resulting in the mean intensity of each color channel of each retinal region taking a predefined specific value, or some geometric normalization, for example rotation normalization, whereby each region is rotated so that its center of mass lies at a specific angle. Thus, for each retinal region $R_k$, block 500 produces the normalized region $R'_k$. Then, in block 510 a CNN is used to classify each region $R'_k$ and produce a classification vector $D_k$. The CNN has been previously trained using a large number of training samples, i.e., training labelled regions. As seen earlier, different embodiments of the invention may employ CNNs trained on only two classes, for example "Healthy" and "Diseased", or more classes, for example "Healthy", "Micro Aneurism", "Hard Exudate" and so on, and, in all cases, the CNN may output $D_k$ as a class probability distribution or as a classification decision vector.

Figure 5:
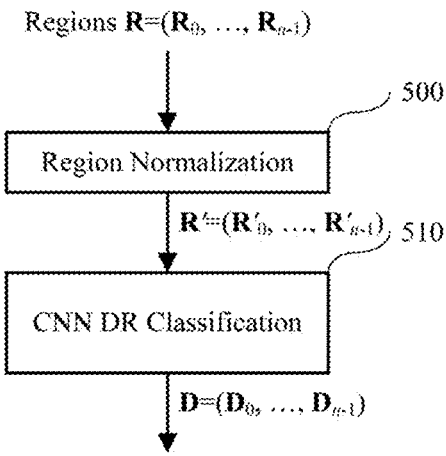
FIGS. 5-23 chow various flowcharts according to respective embodiments of the invention.
Figure 6:
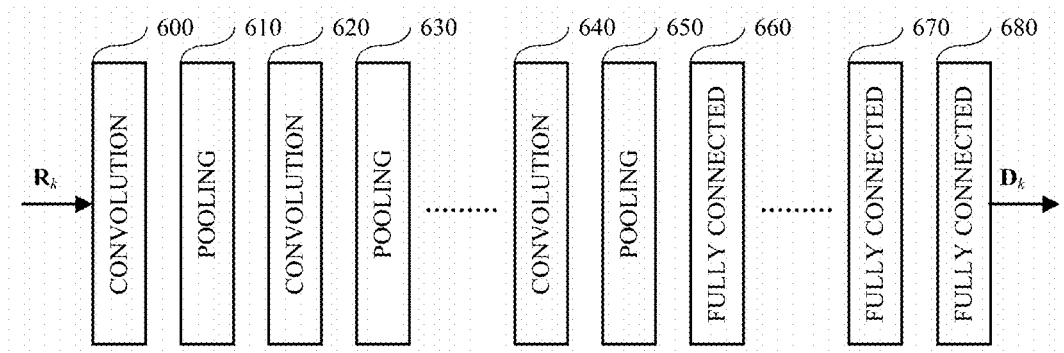

FIG. 6 illustrates the architecture of block 510 of FIG. 5 in more detail. As can be seen in FIG. 6, each region $R_k$ is processed independently to produce its classification vector $D_k$. The CNN of FIG. 6 is a common architecture, employing a number of convolution layers, which convolve their input with learned convolution masks, interleaved with pooling layers, i.e. spatial subsampling layers, followed by a number of fully connected layers to produce the DR lesion classification vector $D_k$ for region $R_k$. The theory of CNNs (en.wikipedia.org/wiki/Convolutional_neural_network) is not covered here but there are numerous publications on the topic, for example Krizhevsky, Alex, Ilya Sutskever, and Geoffrey E. Hinton. "Imagenet classification with deep convolutional neural networks." Advances in neural information processing systems. 2012.

Figure 7:
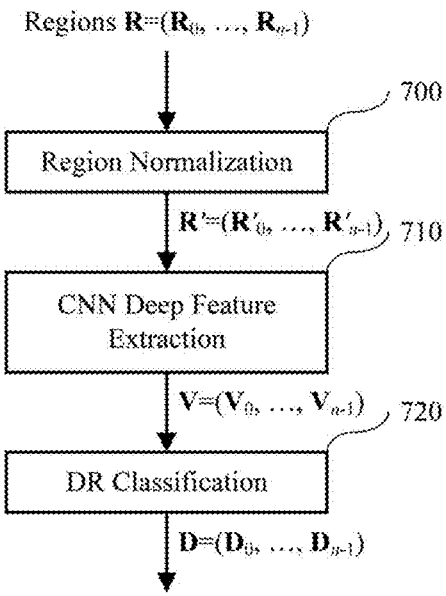

In another embodiment of the invention, block 120 of FIG. 1 comprises the architecture illustrated in FIG. 7. Block 700 is optional and operates in the same fashion as block 500 of FIG. 5. Thus, for each retinal region $R_k$, block 700 produces the normalized region $R'_k$. Then, in block 710 a CNN is used to produce a high-dimensional vector of distinguishing features $V_k$ for each region $R'_k$.

Figure 8:
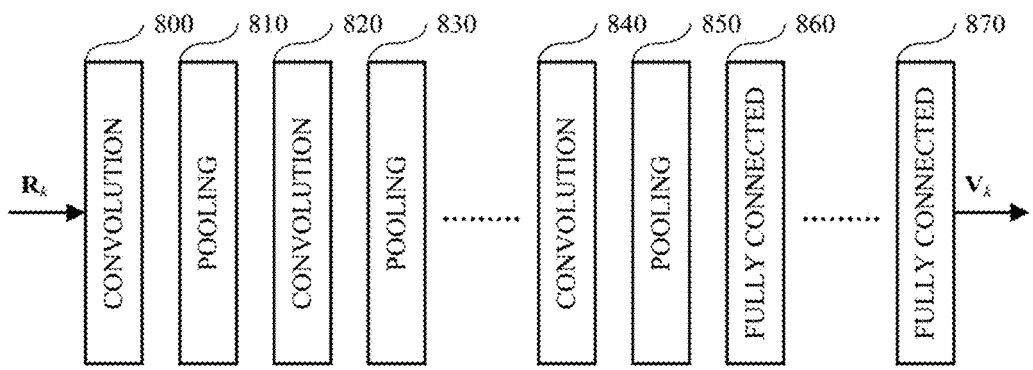

FIG. 8 illustrates the architecture of block 710. As can be seen in FIG. 8, the CNN used to produce the feature vector $V_k$ is the same as the CNN of FIG. 6 with $V_k$ taken at the output of one of the layers preceding the final fully connected classification layer. Then, back to FIG. 7, in block 720 a classifier is used to classify each feature vector $V_k$ and produce a classification vector $D_k$. There are various options for the classifier of block 720, such as a binary or multi-class Support Vector Machine (SVM) or Gradient Boosting Classifier (GBC), previously trained on the feature vectors of a set of training labelled regions. As seen earlier, different embodiments of the invention may employ classifiers trained on two or more classes and may output $D_k$ as a class probability distribution or as a classification decision vector. The theory of SVMs (en.wikipedia.org/wiki/Support_vector_machine) and GBCs (en.wikipedia.org/wiki/Gradient_boosting) are not covered here but there are numerous publications on the topics, for example Burges, Christopher J C. "A tutorial on support vector machines for pattern recognition." Data mining and knowledge discovery 2.2 (1998): 121-167 and Schapire, Robert E., and Yoav Freund. Boosting: Foundations and algorithms. MIT press, 2012.

Figure 9:
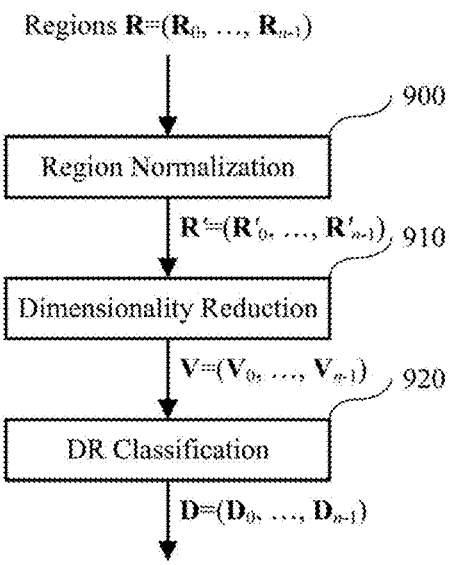

In another embodiment of the invention, block 120 of FIG. 1 comprises the architecture illustrated in FIG. 9. Block 900 is optional and operates in the same fashion as block 500 of FIG. 5 or block 700 of FIG. 7. Thus, for each retinal region $R_k$, block 900 produces the normalized region $R'_k$. Then, in block 910 a dimensionality reduction technique, such as Linear Discriminant Analysis (LDA en.wikipedia.org/wiki/Linear_discriminant_analysis) or Principal Components Analysis (PCA en.wikipedia.org/wiki/Principal_component_analysis), is used to produce a reduced dimensionality representation of each region $R'_k$ which is used as a feature vector $V_k$ for that region. Then, in block 920 a classifier is used to classify each feature vector $V_k$ and produce a classification vector $D_k$. As in the previous embodiment, binary or multi-class SVM or Gradient Boosting Classifier, previously trained on the feature vectors of a set of training labelled regions, are typically good choices for the classifier. As seen earlier, different embodiments of the invention may employ classifiers trained on two or more classes and may output $D_k$ as a class probability distribution or as a classification decision vector.

We now consider the operation of block 130 of FIG. 1. Block 130 of FIG. 1 analyzes all the retinal regions independently and for each region $R_k$ produces a quality classification vector $Q_k=(Q_k^0, \ldots, Q_k^{m-1})$ where m is the number of classes that the classifier of block 130 has been trained on and $Q_k^z$ is the class membership probability of region k for class z. As a first example, in one embodiment of the invention, the classifier in block 130 may be trained to classify regions to m=2 classes, with z=0 the "Good Quality" class label and z=1 the "Bad Quality" class label. As a second example, in a different embodiment of the invention, the classifier in block 130 may be trained to classify regions to m>2 classes, with z=0 the "Good Quality" class label, z=1 the "Bad Illumination" class label, z=2 the "Bad Contrast" class label, . . . , z=m−1 the "Lens Flare" class label.

Thus, in such an embodiment, different types of quality artifacts and imaging artifacts that may be present in the retinal fundus image are assigned separate class labels. Various embodiments of the invention may employ classifiers trained on different numbers of classes to achieve the highest possible performance in assessing the quality of retinal regions. It should be noted that choice of the number of classes for the region quality classifier is independent from the choice of the number of classes for the DR lesion classifier. In all cases, in alternative embodiments of the invention, the classifier in block 130 may be configured to output $Q_k^z$ as a binary 0 or 1 value rather than a class membership probability, in which case $Q_k$ is not a class probability distribution but a classification decision vector.

Figure 10:
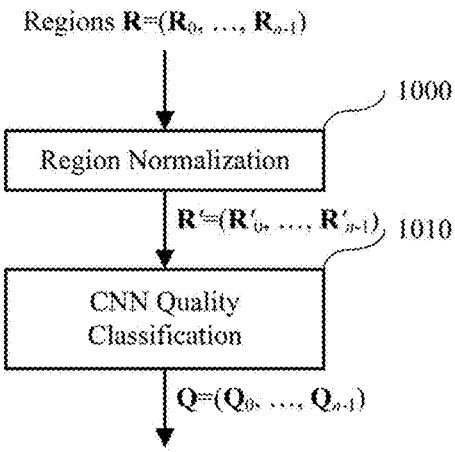

We now consider the architecture of block 130 of FIG. 1 in more detail. In one embodiment of the invention, block 130 of FIG. 1 comprises the architecture illustrated in FIG. 10. In block 1000, retinal regions are optionally normalized. This optional normalization may, for example, involve intensity or geometric normalizations. Thus, for each retinal region $R_k$, block 1000 produces the normalized region $R'_k$. Then, in block 1010 a CNN is used to classify each region $R'_k$ according to its quality and produce a quality classification vector $Q_k$. The CNN has been previously trained using a large number of training samples, i.e., training labelled regions. As seen earlier, different embodiments of the invention may employ CNNs trained on only two classes, for example "Good Quality" and "Bad Quality", or more classes, for example "Good Quality", "Bad Illumination", "Bad Contrast" and so on, and, in all cases, the CNN may output $Q_k$ as a class probability distribution or as a classification decision vector.

Figure 11:
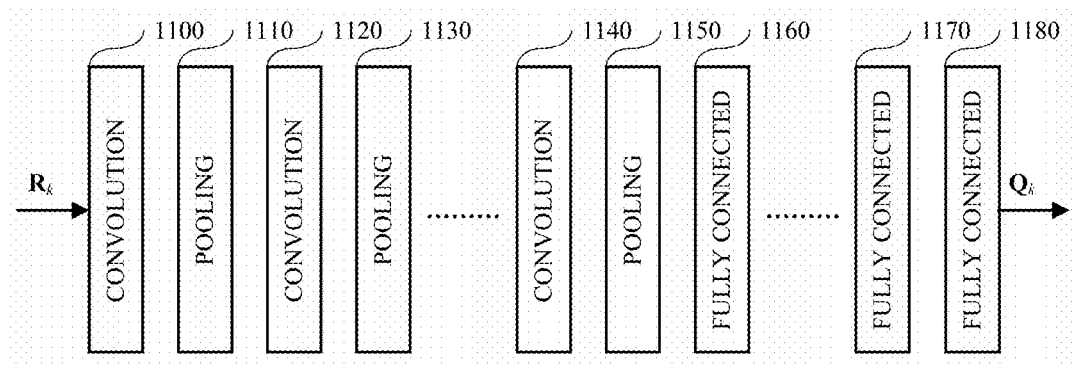

FIG. 11 illustrates the internal architecture of the CNN of block 1010; this is substantially the same as the CNN architecture of FIG. 6 described earlier, although network parameters such as the size, stride and number of filters, the learned convolution masks, the number or convolution layers, the number of fully connected layers and so on may be different.

Figure 12:
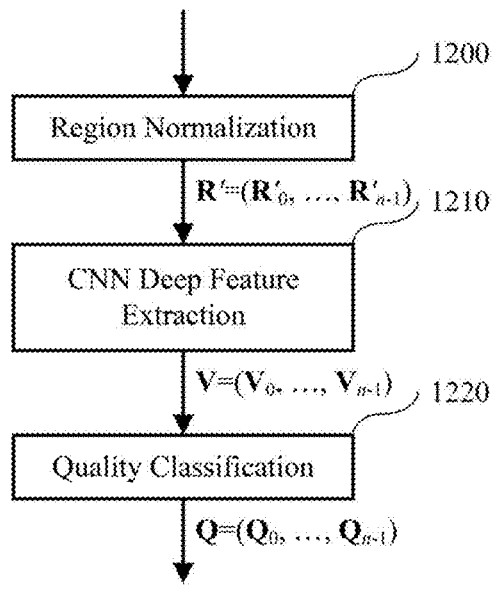

In another embodiment of the invention, block 130 of FIG. 1 comprises the architecture illustrated in FIG. 12. Block 1200 is optional and operates in the same fashion as block 1000 of FIG. 10. Thus, for each retinal region $R_k$, block 1200 produces the normalized region $R'_k$. Then, in block 1210 a CNN is used to produce a high-dimensional vector of distinguishing features $V_k$ for each region $R'_k$.

Figure 13:
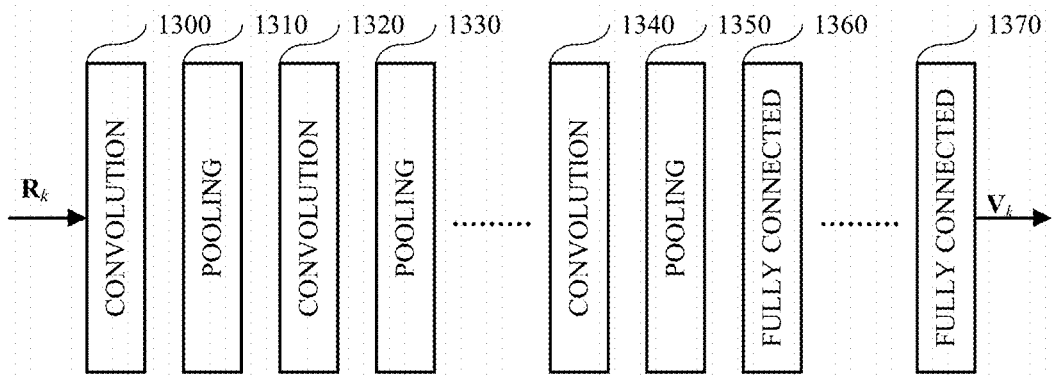

FIG. 13 illustrates the internal architecture of this CNN. As can be seen in FIG. 13, the CNN used to produce the feature vector $V_k$ is the same as the CNN of FIG. 11 with $V_k$ taken at the output of one of the layers preceding the final fully connected classification layer. Then, back to FIG. 12, in block 1220 a classifier is used to classify each feature vector $V_k$ and produce a classification vector $Q_k$. This classifier may, for example, be a binary or multi-class SVM or GBC, previously trained on the feature vectors of a set of training labelled regions. As seen earlier, different embodiments of the invention may employ classifiers trained on two or more classes and may output $Q_k$ as a class probability distribution or as a classification decision vector.

Figure 14:
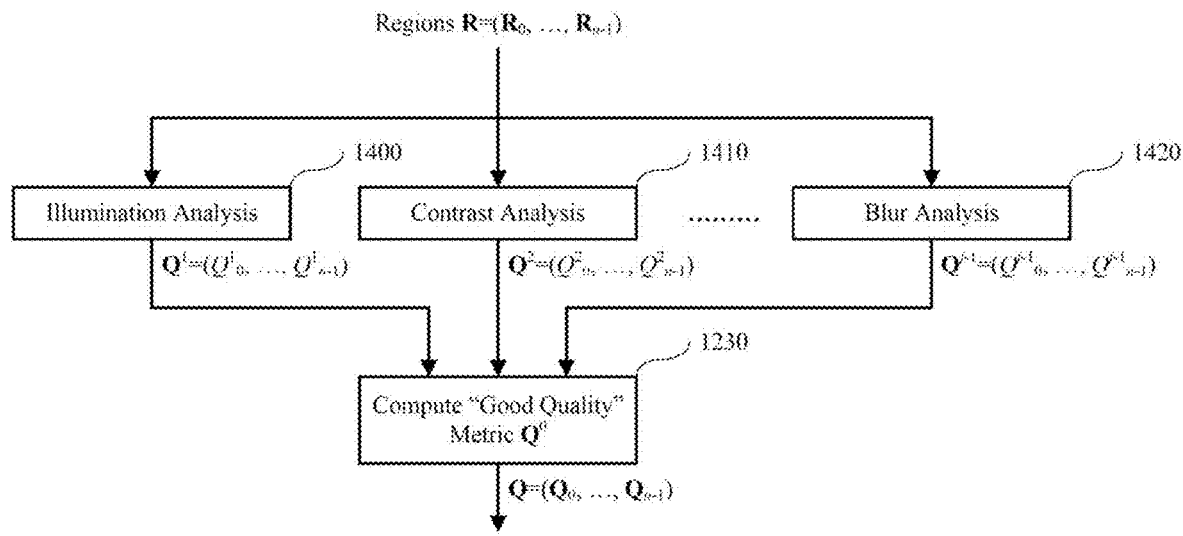

In another embodiment of the invention, block 130 of FIG. 1 comprises the architecture illustrated in FIG. 14. As can be seen in FIG. 14, different techniques are employed to assess the quality of each region $R_k$ according to different criteria, including but not limited to illumination, contrast, blur, etc. Various well known image processing techniques may be employed to perform this region quality analysis. The illumination quality metric of block 1400 may, for example, be calculated as $\min(\mathrm{abs}((\tau_H+\tau_L-2f)/(\tau_H-\tau_L)), 1) \in [0,1]$ where f denotes the average region intensity and $\tau_L$ and $\tau_H$ the lowest and highest acceptable intensity for a region, respectively. The contrast quality metric of block 1410 may be calculated using a suitable technique, for example one of the techniques described in Tripathi, Abhishek Kumar, Sudipta Mukhopadhyay, and Ashis Kumar Dhara. "Performance metrics for image contrast." Image Information Processing (ICIIP), 2011 International Conference on. IEEE, 2011, normalized to [0,1]. Similarly, the blur quality metric of block 1420 may be calculated using a suitable technique, for example the technique described in Marziliano, Pina, et al. "A no-reference perceptual blur metric." Image Processing. 2002. Proceedings. 2002 International Conference on. Vol. 3. IEEE, 2002, normalized to [0,1].

Finally, block 1430 computes a "Good Quality" metric based on the illumination, contract, blur, etc. metrics, for example as $Q_k^0 = 1 - \max(Q_k^1, Q_k^2, \ldots, Q_k^{j-1})$ and produces the final quality assessment vector $Q_k$ for each region $R_k$.

We now consider the operation of block 140 of FIG. 1. Block 140 of FIG. 1 analyzes the DR lesion classification vectors $D_k$ and quality classification vectors $Q_k$ and produces conditioned DR lesion classification vectors $D''_k$. This operation entails three main steps, namely: (1) DR lesion classification vector spatial probability adjustment. This step is optional. Each DR lesion classification vector $D_k$ corresponds to a retinal region $R_k$ and, as seen earlier, each $R_k=R(x,y)$ is retinal region centered on pixel (x,y) of normalized image I'. Thus, for each DR lesion classification vector $D_k$ corresponding to a retinal region $R_k$ centered on pixel (x,y) of I' it is possible to adjust the values of $D_k$ based on the DR lesion classification vectors of its surrounding regions, for example those centered within a distance d of (x,y). This adjustment may, for example, take the form of mean filtering, median filtering, etc. and is beneficial in creating more robust and reliable DR lesion classification vectors for a retinal fundus image. (2) Quality classification vector probability adjustment. This step is optional. The principle of this identical to step (1) above, but the operation are performed on the quality classification vectors Q. (3) DR lesion classification vector adjustment based on quality classification vectors.

Figure 15:
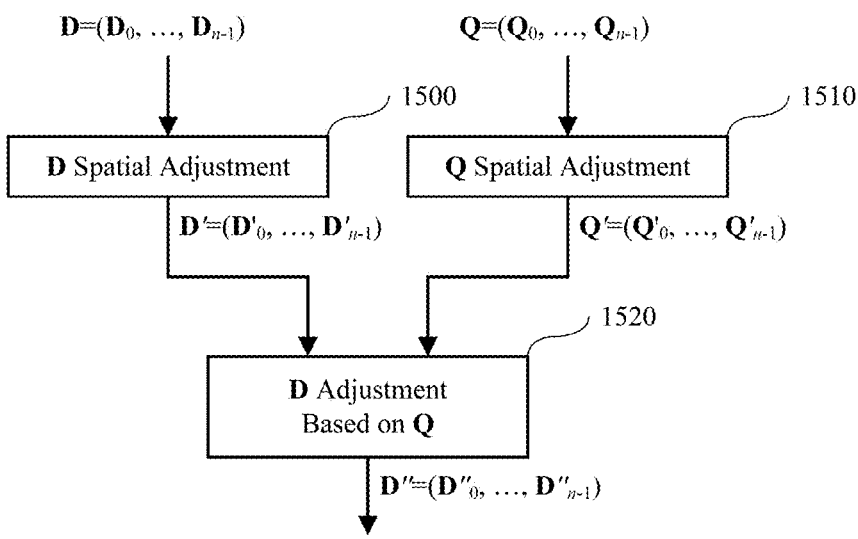

We now consider the architecture of block 140 of FIG. 1 in more detail. FIG. 15 illustrates the architecture of block 140 of FIG. 1. Block 1500 implements DR lesion classification vector spatial probability adjustment. That is, for each DR lesion classification vector $D_k$ corresponding to a retinal region $R_k$ centered on pixel (x,y) of I', the values of $D_k$ are adjusted based on the DR lesion classification vectors of its surrounding regions centered within a distance d of (x,y). This adjustment may, for example, take the form of mean, median, min, max or other filtering, to produce adjusted DR lesion classification vector $D'_k$. An alternative way of viewing this is as follows: For image I', l spatial probability maps may be produced, where l is the number of DR classification labels in D. For example, for l=2 classes, with c=0 the "Healthy" class label and c=1 the "Diseased" class label, a "Healthy" probability map $^{DR}P^c$ and a "Diseased" probability map $^{DR}P^1$ may be produced. Then, for each DR lesion classification vector $D_k$ corresponding to a retinal region $R_k$ centered on pixel (x,y) of I', $^{DR}P^c(x/s,y/s)=D_k^c$ where s is the sampling stride used in region extraction. Each $^{DR}P^c$ may then be spatially processed, e.g. with a mean, median, min, max or other filter, or other morphological operations, such as dilation, erosion, etc. to produce adjusted probability maps $^{DR}P'^c$, which may then be mapped to adjusted DR lesion classification vectors $D'_k$. In a similar fashion to block 1500, block 1510 implements quality classification vector spatial probability adjustment. Finally, block 1520 of FIG. 15 performs DR lesion classification vector adjustment based on quality classification vectors. There are various possibilities in how this adjustment may be performed.

As one example, for each $D'_k$ and for each class label c out of l DR classes, this adjustment may be performed as $$D_k''^c = \begin{cases} D_k'^c & \text{if } Q_k'^0 \geq 0.5 \\ 0 & \text{if } Q_k'^0 < 0.5 \end{cases}$$

where $Q'^0_k$ denotes the "Good Quality" class probability for region $R_k$. In essence, with the above relation, if the "Good Quality" class probability for region $R_k$ is less than 0.5, all DR classification vector probabilities for region $R_k$ are reduced to 0, i.e. the system does not deliver any DR classification probabilities for that region because the quality is too poor.

As another example, for each $D'_k$ and for each class label c out of l DR classes, this adjustment may be performed as $$D_k''^c = \begin{cases} D_k'^c & \text{if } Q_k'^0 \geq 0.5 \\ (Q_k'^0 + 0.25)D_k'^c & \text{if } 0.5 > Q_k'^0 \geq 0.25 \\ 0 & \text{if } Q_k'^0 < 0.5 \end{cases}$$

where $Q_k'^0$ denotes the "Good Quality" class probability for region $R_k$. With this relation, the drop off in the DR classification probabilities down to 0 due to poor quality is more gradual.

In the examples above, each $D_k'$ is adjusted based on the corresponding $Q_k'$. In alternative embodiments of the invention, each $D_k'$ corresponding to a retinal region $R_k$ centered on pixel (x,y) of I' may be adjusted based on the corresponding $Q_k'$ as well as the quality classification vectors of surrounding regions, for example those centered within a distance d of (x,y).

We now consider the operation of block 150 of FIG. 1. Block 150 of FIG. 1 analyzes the DR lesion classification vectors D" and produces a final retinal fundus image-level DR classification vector $C=(C^0, \ldots, C^{w-1})$ where w is the number of classes and $C^v$ is the class membership probability for class v. In one embodiment of the invention, w=2 with v=0 the "Healthy" class label and v=1 the "Diseased" class label. As a second example, in a different embodiment of the invention, w=4 classes, with each class corresponding to DR medical grade. In all cases, in alternative embodiments of the invention, $C^v$ may take a binary 0 or 1 value, in which case C is not a class probability distribution but a classification decision vector.

Figure 16:
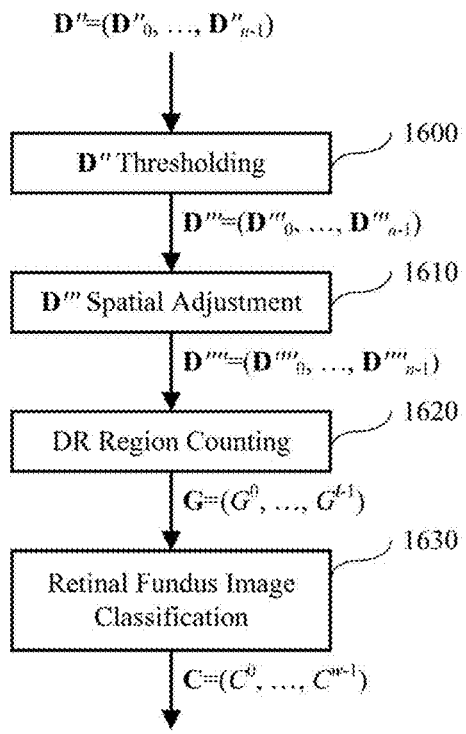

We now consider the architecture of block 150 of FIG. 1 in more detail. In one embodiment of the invention, block 150 of FIG. 1 comprises the architecture of FIG. 16. In block 1600 of FIG. 16, the DR lesion classification vector probabilities are thresholded, for example as $$D_k'''^c = \begin{cases} 1 & \text{if } D_k''^c \geq \tau_D^c \\ 0 & \text{if } D_k''^c < \tau_D^c \end{cases}$$

Then, in block 1610, the D''' undergoes spatial processing to produce D''''. This block operates in substantially the same fashion as block 1500 of FIG. 15, performing operations such as median filtering, erosion, dilation, and so on. In alternative embodiments of the invention, block 1610 may be skipped, while in different embodiments of the invention the order of blocks 1600 and 1610 may be reversed. Then, in block 1620, the number of regions for each class label l in D'''' is counted. As seen earlier, in some embodiments of the invention, l=2 classes, with c=0 the "Healthy" class label and c=1 the "Diseased" class label. In different embodiments of the invention, l>2 classes, with c=0 the "Healthy" class label, c=1 the "Micro Aneurism" class label, c=2 the "Hard Exudate" class label, . . . , c=l−1 the "Laser Scar" class label. Thus, block 1620 produces a vector $G=(G^0, \ldots, G^{l-1})$ where each element $G^c$ is a region count for the corresponding label c. Then, based on the region count vector G, block 1630 produces a final retinal fundus image classification decision vector $C=(C^0, \ldots, C^{w-1})$ where w is the number of classes and $C^v$ is the decision for class v. As seen earlier, in one embodiment of the invention, w=2 with v=0 the "Healthy" class label and v=1 the "Diseased" class label. In a different embodiment of the invention, w=4 classes, with each class corresponding to DR medical grade, which can be established based on the numbers of different types of DR lesions in the retinal fundus image.

Figure 17:
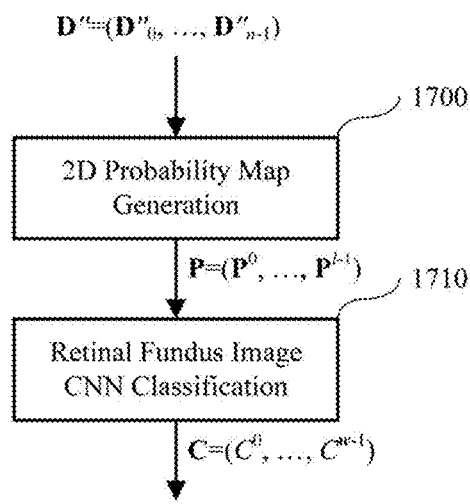
Figure 18:
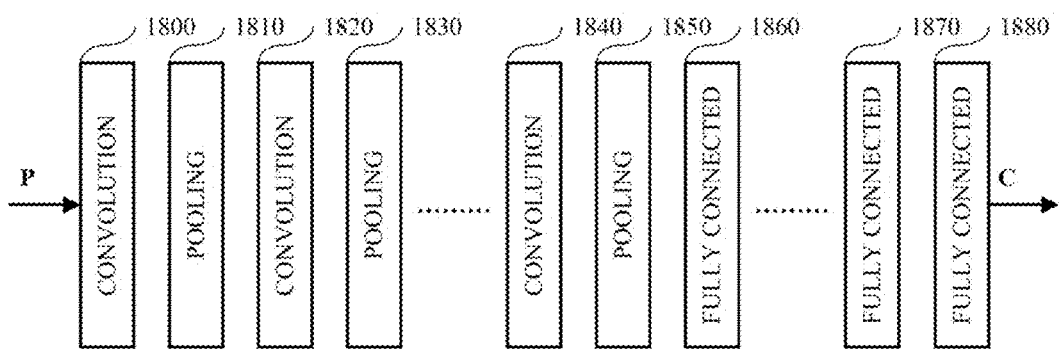

In another embodiment of the invention, block 150 of FIG. 1 comprises the architecture of FIG. 17. In block 1700 of FIG. 17, the DR lesion classification vectors D" are converted into l 2D probability maps, where l is the number of DR classification labels in D". The process of converting a vector of DR classification vectors into 2D probability maps is substantially the same as described earlier for block 1500 of FIG. 15. In creating the 2D probability maps, block 1700 may optionally (i) change the dynamic range of the probabilities, for example from a real range of [0,1] to an integer range [0,255], and (ii) subsample the 2D probability maps to fixed resolution of txt pixels, for example t=256 pixels. Thus, block 1700 generates l 2D probability maps $P=(P^0, \ldots, P^{l-1})$. Then in block 1710 a CNN is used to classify the probability maps P and produce a final retinal fundus image-level DR classification vector $C=(C^0, \ldots, C^{w-1})$ where w is the number of classes and $C^v$ is the class membership probability for class v. The CNN has been previously trained using a large number of training samples. As seen earlier, different embodiments of the invention may employ CNNs trained on different number of classes, for example w=2 with v=0 the "Healthy" class label and v=1 the "Diseased" class label, or w=4 classes, with each class corresponding to DR medical grade. In all cases, in alternative embodiments of the invention, $C^v$ may take a binary 0 or 1 value, in which case C is not a class probability distribution but a classification decision vector. FIG. 18 illustrates the internal architecture of the CNN of block 1710; this is substantially the same as the CNN architectures of FIG. 6 and FIG. 11 described earlier, although network parameters such as the size, stride and number of filters, the learned convolution masks, the number or convolution layers, the number of fully connected layers and so on may be different.

Figure 19:
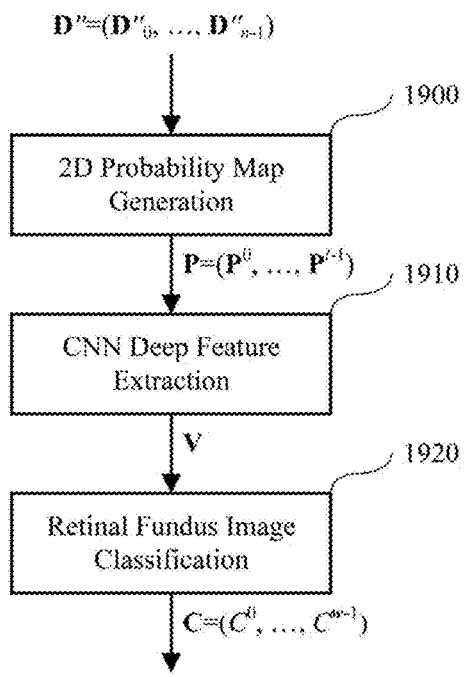
Figure 20:
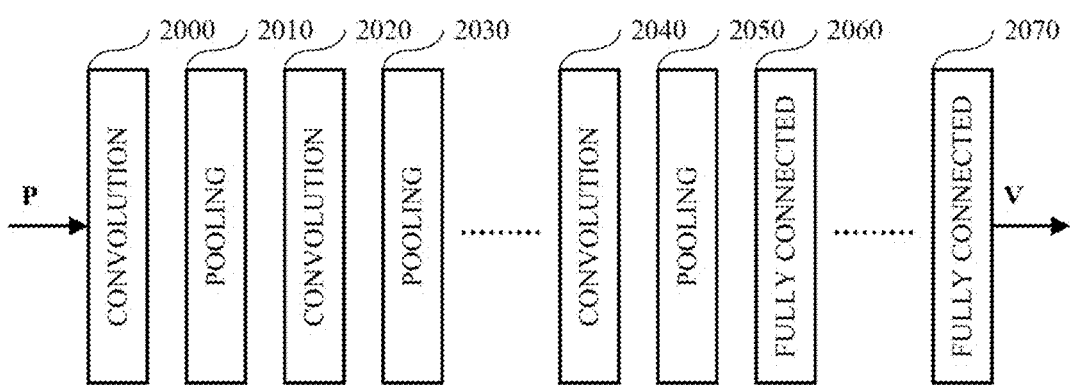

In another embodiment of the invention, block 150 of FIG. 1 comprises the architecture illustrated in FIG. 19. Block 1900 operates in the same fashion as block 1700 of FIG. 17. Then, in block 1910 a CNN is used to produce a high-dimensional vector of distinguishing features V. FIG. 20 illustrates the internal architecture illustrates the internal architecture of this CNN. As can be seen in FIG. 20, the CNN used to produce the feature vector V is the same as the CNN of FIG. 18 with V taken at the output of one of the layers preceding the final fully connected classification layer. Then, back to FIG. 19, in block 1920 a classifier is used to classify the feature vector V and produce the classification vector C. This classifier may, for example, be a binary or multi-class SVM or Gradient Boosting Classifier, previously trained on the feature vectors of a set of training samples. As seen earlier, different embodiments of the invention may employ classifiers trained on two or more classes and may output C as a class probability distribution or as a classification decision vector.

Figure 21:
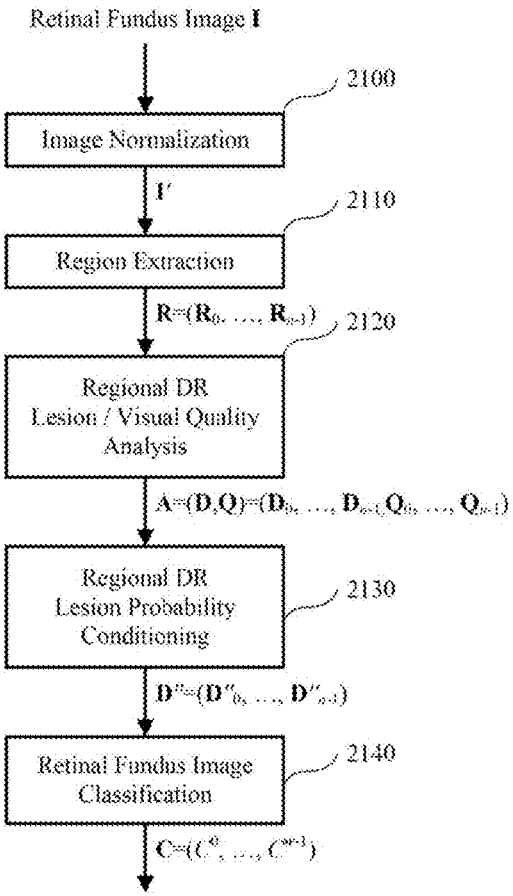

FIG. 21 illustrates an alternative embodiment of the invention. There, blocks 2100 and 2110 operate in substantially the same fashion as blocks 100 and 110 of FIG. 1, performing image normalization and region extraction.

We now consider the operation of block 2120 of FIG. 21. Block 2120 of FIG. 21 analyzes all the retinal regions independently and for each region $R_k$ produces a joint DR lesion/quality classification vector $A_k=(D_k, Q_k)=(D_k^0, \ldots, D_k^{l-1}, Q_k^0, \ldots, Q_k^{m-1})$ where l is the number of DR lesion classes as described previously and m is the number of region quality classes as described previously. Thus, in the training of the classifier of block 2120, each training sample is assigned both a DR lesion class label and a quality class label, allowing the classifier to produce a joint DR lesion/quality classification vector $A_k=(D_k, Q_k)=(D_k^0, \ldots, D_k^{l-1}, Q_k^0, \ldots, Q_k^{m-1})$ for each region $R_k$. As seen previously, the classifier in block 2120 may be configured to output binary 0 or 1 value rather than class membership probabilities.

Figure 22:
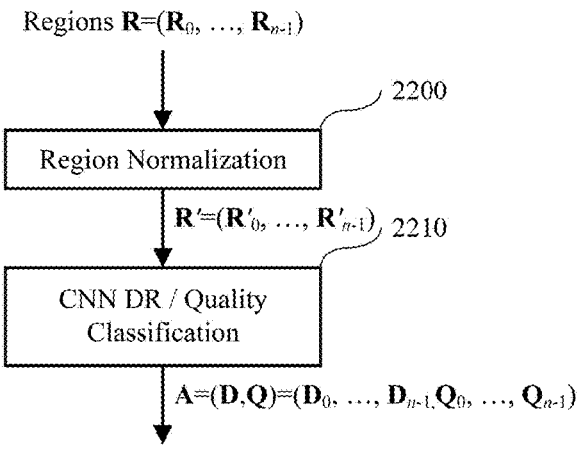
Figure 23:
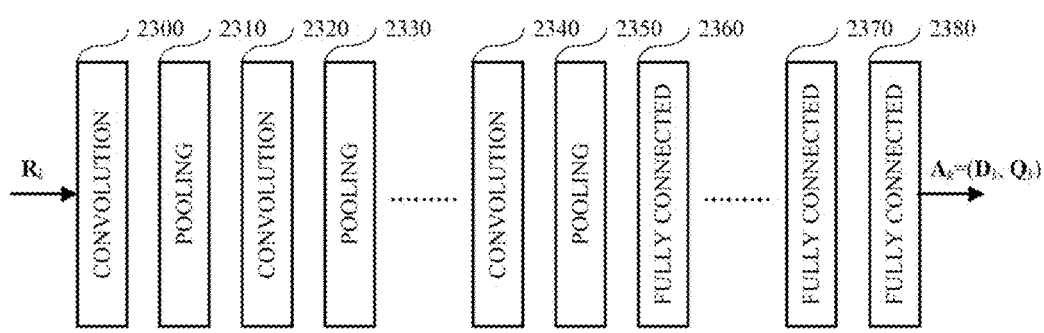

We now consider the architecture of block 2120 of FIG. 21 in more detail. Block 2120 of FIG. 21 comprises the architecture illustrated in FIG. 22. Block 2200 performs retinal region normalization in substantially the same fashion as block 500 or FIG. 5 and block 700 or FIG. 7. Thus, for each retinal region $R_k$, block 2200 produces the normalized region $R'_k$. Then, in block 2210 a CNN is used to classify each region $R'_k$ and produce the classification vector $A_k$. FIG. 23 illustrates the architecture of block 2210 of FIG. 22 in more detail. This is substantially the same as the CNN architecture of FIG. 6 and FIG. 11 described earlier, although network parameters such as the size, stride and number of filters, the learned convolution masks, the number or convolution layers, the number of fully connected layers and so on may be different.

Then, back to FIG. 21, block 2130 performs regional DR lesion probability conditioning in substantially the same fashion as block 140 of FIG. 1, and block 2140 performs retinal fundus image classification in substantially the same fashion as block 150 of FIG. 1.

In some embodiments, the process of imaging is performed by a computing system. In some embodiments, the computing system includes one or more computing devices, for example, a personal computer that is IBM, Macintosh, Microsoft Windows or Linux/Unix compatible or a server or workstation. In one embodiment, the computing device comprises a server, a laptop computer, a smart phone, a personal digital assistant, a kiosk, or a media player, for example. In one embodiment, the computing device includes one or more CPUS, which may each include a conventional or proprietary microprocessor. The computing device further includes one or more memory, such as random access memory ("RAM") for temporary storage of information, one or more read only memory ("ROM") for permanent storage of information, and one or more mass storage device, such as a hard drive, diskette, solid state drive, or optical media storage device. Typically, the modules of the computing device are connected to the computer using a standard based bus system. In different embodiments, the standard based bus system could be implemented in Peripheral Component Interconnect (PCI), Microchannel, Small Computer System Interface (SCSI), Industrial Standard Architecture (ISA) and Extended ISA (EISA) architectures, for example. In addition, the functionality provided for in the components and modules of computing device may be combined into fewer components and modules or further separated into additional components and modules.

The computing device is generally controlled and coordinated by operating system software, such as Windows XP, Windows Vista, Windows 7, Windows 8, Windows Server, Embedded Windows, Unix, Linux, Ubuntu Linux, SunOS, Solaris, iOS, Blackberry OS, Android, or other compatible operating systems. In Macintosh systems, the operating system may be any available operating system, such as MAC OS X. In other embodiments, the computing device may be controlled by a proprietary operating system. Conventional operating systems control and schedule computer processes for execution, perform memory management, provide file system, networking, I/O services, and provide a user interface, such as a graphical user interface (GUI), among other things.

The exemplary computing device may include one or more commonly available I/O interfaces and devices, such as a keyboard, mouse, touchpad, touchscreen, and printer. In one embodiment, the I/O interfaces and devices include one or more display devices, such as a monitor or a touchscreen monitor, that allows the visual presentation of data to a user. More particularly, a display device provides for the presentation of GUIs, application software data, and multimedia presentations, for example. The computing device may also include one or more multimedia devices, such as cameras, speakers, video cards, graphics accelerators, and microphones, for example. The I/O interfaces and devices provide a communication interface to various external devices. The computing device is electronically coupled to a network, which comprises one or more of a LAN, WAN, and/or the Internet, for example, via a wired, wireless, or combination of wired and wireless, communication link. The network communicates with various computing devices and/or other electronic devices via wired or wireless communication links.

Images to be processed according to methods and systems described herein, may be provided to the computing system over the network from one or more data sources. The data sources may include one or more internal and/or external databases, data sources, and physical data stores. The data sources may include databases storing data to be processed with the imaging system according to the systems and methods described above, or the data sources may include databases for storing data that has been processed with the imaging system according to the systems and methods described above. In some embodiments, one or more of the databases or data sources may be implemented using a relational database, such as Sybase, Oracle, CodeBase, MySQL, SQLite, and Microsoft® SQL Server, as well as other types of databases such as, for example, a flat file database, an entity-relationship database, a relational database, and object-oriented database, NoSQL database, and/or a record-based database.

The computing system includes an imaging system module that may be stored in the mass storage device as executable software codes that are executed by the CPU. These modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The computing system is configured to execute the imaging system module in order to perform, for example, automated low-level image processing, automated image registration, automated image assessment, automated screening, and/or to implement new architectures described above.

In general, the word "module," as used herein, refers to logic embodied in hardware or firmware, or to a collection of software instructions, possibly having entry and exit points, written in a programming language, such as, for example, Python, Java, Lua, C and/or C++. Software modules may be provided on a computer readable medium, such as a optical storage medium, flash drive, or any other tangible medium. Such software code may be stored, partially or fully, on a memory device of the executing computing device, such as the computing system, for execution by the computing device. Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The term "including" means "included but not limited to." The term "or" means "and/or".

Any process descriptions, elements, or blocks in the flow or block diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by the computing system and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. For example, a feature of one embodiment may be used with a feature in a different embodiment. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

What is claimed is:

1. A method of classifying eye images, comprising:
normalizing and segmenting a received eye image into a normalized and segmented plurality of regular regions;
automatically determining an eye disease vector for each of the plurality of regions with at least one classifier comprising a neural network;
automatically annotating each of the respective plurality of regions, based on the determined eye disease vectors; and
automatically determining a grade of the received eye image with respect to at least two grades, dependent on a probability of a type I error of the grade, and a probability of a type II error of the grade, based on at least the annotations,
wherein the neural network is trained based on at least an expert annotation of respective regions of eye images, according to at least one objective classification criterion.

2. The method according to claim 1, wherein the neural network comprises a plurality of hidden layers.

3. The method according to claim 2, wherein the neural network comprises a deep neural network.

4. The method according to claim 1, wherein the neural network comprises a deep convolutional neural network.

5. The method according to claim 1, wherein the neural network comprises a recurrent neural network, further comprising receiving a second vascular image acquired at a time different from the vascular image; and outputting information dependent on at least a change in the eye image over time.

6. The method according to claim 1, further comprising receiving at least an expert annotation of a quality of respective regions of a retinal image.

7. The method according to claim 1, wherein the at least one classifier comprises a multi-class support vector machine classifier.

8. The method according to claim 1, wherein the at least one classifier comprises a Gradient Boosting Classifier.

9. The method according to claim 1, wherein the at least one classifier classifies a respective region based on the eye disease vectors of a plurality of respective regions.

10. The method according to claim 1, wherein the at least one classifier classifies a respective region based on the eye disease vectors of a plurality of contiguous regions.

11. The method according to claim 1, wherein the at least one classifier comprises a classifier for determining a region having indicia of diabetic retinopathy.

12. The method according to claim 11, wherein the grade comprises a degree of diabetic retinopathy with respect to at least three different grades.

13. The method according to claim 1, further comprising outputting an image representing the classification of regions of the eye image.

14. The method according to claim 1, wherein the eye images comprise funduscopic images, and the annotations comprise at least an indication of diabetic retinopathy within a respective region of a respective funduscopic image.

15. A system for classifying eye images, comprising:
an input configured to receive at least one eye image;
a memory configured to store information defining a neural network trained based on at least an expert annotation of respective regions of a plurality of retinal images, according to at least one objective classification criterion;
at least one automated processor, configured to:
normalize and segment the eye image into a plurality of regular regions;
determine an eye disease vector for each of the plurality of regions of the eye image with at least one classifier comprising the defined neural network;
annotate each of the respective plurality of regions, based on the determined eye disease vectors;
grade the received eye image with respect to at least two grades, based on at least the annotations; and
determine a probability of correctness of the grade dependent on a probability of a type I error of the grade and a probability of a type II error of the grade; and
an output configured to communicate the grade.

16. The system according to claim 15, wherein the neural network comprises a deep neural network having a plurality of hidden layers.

17. The system according to claim 15, wherein the neural network comprises a recurrent neural network, the input being further configured to receive a second eye image acquired at a time different from the eye image; and the at least one automated processor being further configured to analyze at least a change in the eye image over time.

18. The method according to claim 15, wherein the neural network comprises a recurrent neural network, the grade comprises a severity of diabetic retinopathy, and the grade is selected from at least three different grades.

19. A computer readable medium, storing non-transitory instructions for controlling at least one automated processor, comprising:
instructions for determining a pathology vector relating to existence of pathology in an anatomical region, for each of a plurality of regular portions of a segmented normalized image of the anatomical region, with at least one classifier comprising a neural network trained based on at least an expert annotation of respective portions of segmented normalized images of the anatomical region, according to at least one objective classification criterion for the pathology;
instructions for automatically annotating each of the respective plurality of portions, based on the determined pathology vectors; and
instructions for automatically grading the received image with respect to the pathology based on the automatically annotated respective plurality of portions, with respect to at least two grades and determining a probability of correctness of the grading comprising a probability of a type I error and a probability of a type II error.

20. The computer readable medium according to claim 19, wherein the neural network comprises a recurrent neural network, the pathology comprises diabetic retinopathy, and the grading is with respect to at least three different grades.

* * * * *